(12) United States Patent
Bigner et al.

(10) Patent No.: US 11,065,332 B2
(45) Date of Patent: Jul. 20, 2021

(54) COMBINATION THERAPY OF IMMUNOTOXIN AND CHECKPOINT INHIBITOR

(71) Applicants: DUKE UNIVERSITY, Durham, NC (US); THE GOVERNMENT OF THE UNITED STATES AS REPRESENTED BY THE SECRETARY OF HEALTH AND HUMAN SERVICES, NATIONAL INSTITUTES OF HEALTH, Rockville, MD (US)

(72) Inventors: Darell Bigner, Mebane, NC (US); Vidyalakshmi Chandramohan, Durham, NC (US); Smita Nair, Cary, NC (US); Matthias Gromeier, Durham, NC (US); Xuhui Bao, Durham, NC (US); Ira H. Pastan, Potomac, MD (US)

(73) Assignees: Duke University, Durham, NC (US); The Government of The United States as Represented by the Secretary of Health and Human Services, National Institutes of Health, Rockville, MD (US)

(*) Notice: Subject to any disclaimer, the term of this patent is extended or adjusted under 35 U.S.C. 154(b) by 479 days.

(21) Appl. No.: 15/773,418

(22) PCT Filed: Nov. 4, 2016

(86) PCT No.: PCT/US2016/060469
§ 371 (c)(1),
(2) Date: May 3, 2018

(87) PCT Pub. No.: WO2017/079520
PCT Pub. Date: May 11, 2017

(65) Prior Publication Data
US 2018/0311346 A1 Nov. 1, 2018

Related U.S. Application Data

(60) Provisional application No. 62/250,749, filed on Nov. 4, 2015.

(51) Int. Cl.
*A61K 39/395* (2006.01)
*C07K 16/28* (2006.01)
*C07K 16/30* (2006.01)
*A61K 47/68* (2017.01)
*A61P 35/00* (2006.01)
*A61K 38/16* (2006.01)
*A61K 39/00* (2006.01)

(52) U.S. Cl.
CPC .......... *A61K 39/395* (2013.01); *A61K 38/164* (2013.01); *A61K 39/3955* (2013.01); *A61K 47/6829* (2017.08); *A61K 47/6849* (2017.08); *A61K 47/6851* (2017.08); *A61P 35/00* (2018.01); *C07K 16/2818* (2013.01); *C07K 16/2863* (2013.01); *C07K 16/30* (2013.01); *A61K 2039/505* (2013.01); *A61K 2039/507* (2013.01); *C07K 2317/622* (2013.01); *C07K 2317/624* (2013.01); *C07K 2317/73* (2013.01); *C07K 2317/76* (2013.01); *C07K 2319/55* (2013.01)

(58) Field of Classification Search
None
See application file for complete search history.

(56) References Cited

U.S. PATENT DOCUMENTS

| | | | |
|---|---|---|---|
| 2009/0226910 A1 | 9/2009 | Isac et al. | |
| 2009/0269343 A1 | 10/2009 | Bigner et al. | |
| 2010/0319896 A1 | 12/2010 | Rajaraman | |
| 2013/0022598 A1 | 1/2013 | Bigner et al. | |

FOREIGN PATENT DOCUMENTS

| | | |
|---|---|---|
| JP | 2006521377 A | 9/2006 |
| JP | 2012533619 A | 12/2012 |
| JP | 2013529183 A | 7/2013 |
| JP | 2014513136 A | 5/2014 |
| WO | 2004094409 A1 | 11/2004 |
| WO | 2012151523 A1 | 11/2012 |
| WO | 2015-035112 A1 | 3/2015 |
| WO | 2015-069770 A1 | 5/2015 |
| WO | 2015112900 A1 | 7/2015 |
| WO | 2015117002 A1 | 8/2015 |
| WO | 2015138920 A1 | 9/2015 |

OTHER PUBLICATIONS

Chandramohan et al. (Clinical Cancer Research, vol. 19, No. 17, pp. 4717-4727, 2013) (Year: 2013).*
Wainwright et al. (Clinical Cancer Research, vol. 20, No. 20, pp. 5290-5301,2014) (Year: 2014).*
Nicholas et al. (Brain Tumor Res Treat Apr. 2013; 1(1): 2-8). (Year: 2013).*
Chandramohan, V. et al., 'Construction of an immunotoxin, D2C7-(scdsFv)-PE38KDEL, targeting EGFRwt and EFGRvIII for brain tumor therapy' Clinical Cancer Research, Sep. 1, 2013, vol. 19, No. 17, pp. 4717-4727 See abstract; pp. 4720-4722; and Supplementary Figure S1.

(Continued)

*Primary Examiner* — Meera Natarajan
(74) *Attorney, Agent, or Firm* — Banner & Witcoff, Ltd.

(57) ABSTRACT

Regional, tumor-targeted, cytotoxic therapy, such as D2C7-immunotoxin (D2C7-IT), not only specifically target and destroy tumor cells, but in the process initiate immune events that promote an in situ vaccine effect. The antitumor effects are amplified by immune checkpoint blockade which engenders a long-term systemic immune response that effectively eliminates all tumor cells.

22 Claims, 14 Drawing Sheets

Specification includes a Sequence Listing.

(56) References Cited

OTHER PUBLICATIONS

Wainwright, D. A. et al., 'Durable therapeutic efficacy utilizing combinatorial blockade against IDO, CTLA-4, and PD-L1 in mice with brain tumors' Clinical Cancer Research, Oct. 15, 2014, vol. 20, No. 20, pp. 5290-5301, NIH-PA Author Manuscript version (Internal pp. 1-23) See abstract; and pp. 5-6.

Zhu, Y. et al., 'CSF1/CSF1R blockade reprograms tumor-infiltrating macrophages and improves response to T-cell checkpoint immunotherapy in pancreatic cancer models' Cancer Research, Sep. 15, 2014, vol. 74, No. 18, pp. 5057-5069 See abstract; and p. 5058.

International Search Report for PCT/US2016/060469 [dated Feb. 16, 2017].

May 16, 2019—(JP) Notice of Reasons for Rejection—App. 2018-543049—Eng Tran.

Leshem et al. "Combining anti-CTLA4 with RG7787, an immunotoxin targeting mesothelin, promotes tumor eradication" Journal ofor Immunotherapy of Cancer, vol. 3, No. 2, Nov. 4, 2015, pp. 1-2.

MacDonald et al. "A phase I clinical study of VB4-845: weekly intratumoral administration of an anti-EpCAM recombinant fusion protein in patients with squamous cell carcinoma of the head and neck" Drug Design, Development and Therapy, Jan. 1, 2009, pp. 105-114.

Pastan et al. "Immunotoxin therapy of cancer" Nature Reviews, vol. 6, No. 7, Jul. 1, 2006, pp. 559-565.

Apr. 30, 2019—(EP) Extended European Search Report—App. 16863025.9.

\* cited by examiner

Fig. 3.

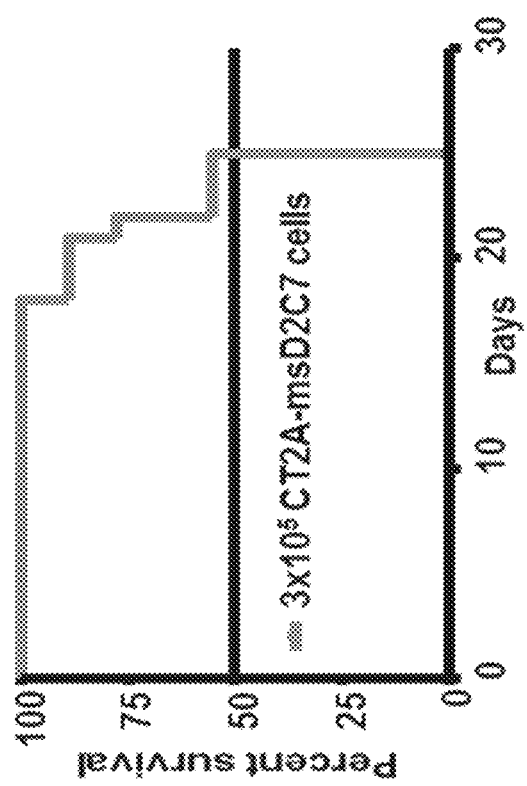

Experimental outline for D2C7-IT, BLZ945 combination therapy.

Anti-tumor efficacy of D2C7-IT and BLZ945 combination therapy against the intracranial CT2A-mD2C7 glioma model.

Figs. 9A-9B
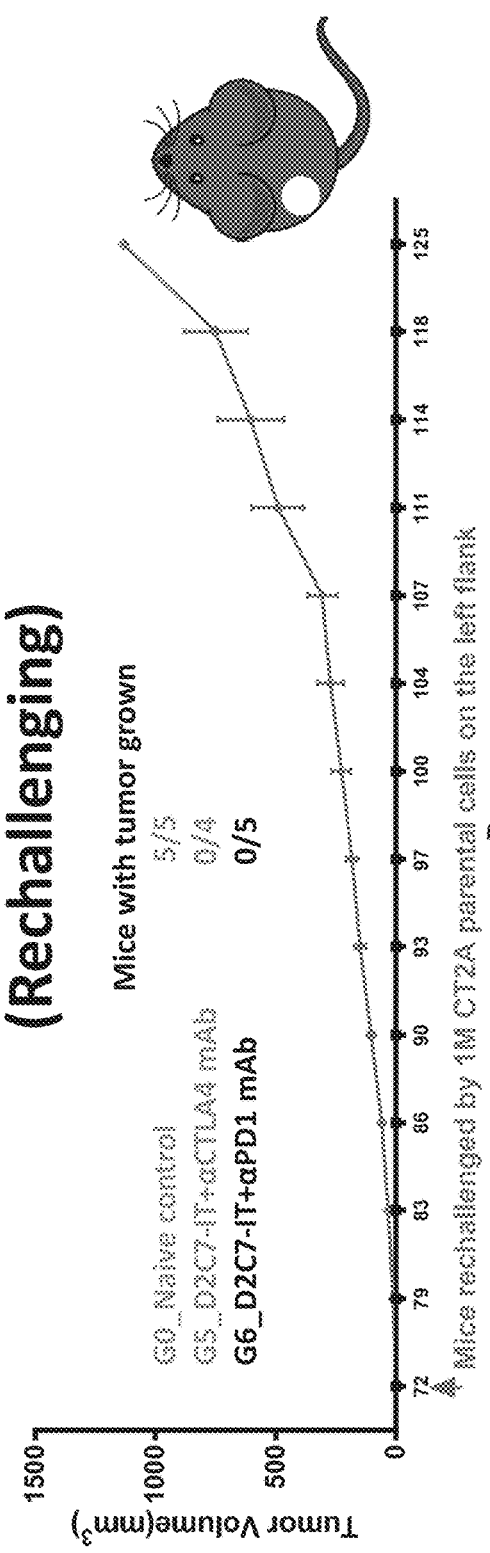
Fig. 9A
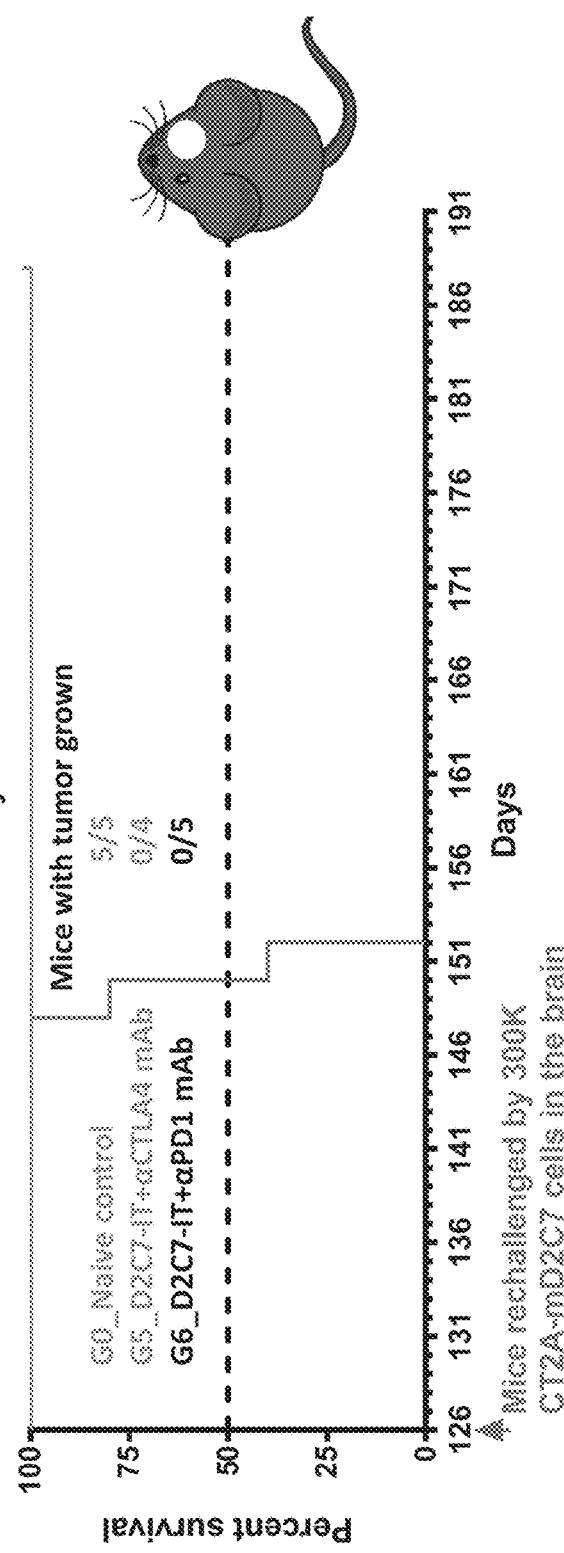
Fig. 9B

COMBINATION THERAPY OF IMMUNOTOXIN AND CHECKPOINT INHIBITOR

This invention was made with government support under CA197264 and CA-154291 awarded by the National Institutes of Health. The government has certain rights in the invention.

TECHNICAL FIELD OF THE INVENTION

This invention is related to the area of immunotherapy. In particular, it relates to combination regimens for treating tumors and kits and medicaments for accomplishing them.

BACKGROUND OF THE INVENTION

Glioblastoma is the most dismal malignant brain tumor among all primary brain and central nervous system tumors. The median survival time for glioblastoma patients with the current standard treatment or even newly developed agents is less than 15 months. Thus, there is an urgent need to develop advanced and efficient therapeutic approaches to improve the poor survival outlook of glioblastoma patients as well as other tumors expressing EGFR receptors.

SUMMARY OF THE INVENTION

According to one aspect of the invention a method is provided for treating a tumor in a patient. An immunotoxin and an immune checkpoint inhibitor are administered to the patient. The immunotoxin comprises a single chain variable region antibody fused to a PE38 truncated *Pseudomonas* exotoxin. The single chain variable region antibody has CDR1, CDR2, and CDR3 regions as shown in SEQ ID NO: 6-11.

According to another aspect of the invention a kit is provided for treating a tumor. The kit comprises an immunotoxin and an immune checkpoint inhibitor. The immunotoxin comprises a single chain variable region antibody fused to a PE38 truncated *Pseudomonas* exotoxin, wherein the single chain variable region antibody has CDR1, CDR2, and CDR3 regions as shown in SEQ ID NO: 6-11;

These and other embodiments which will be apparent to those of skill in the art upon reading the specification provide the art with treatment methods, regimens, kits, and agents for treating glioblastomas and other tumors expressing epidermal growth factor (EGF) receptors i.e., EGFR and its mutants, e.g., EGFR variant m.

BRIEF DESCRIPTION OF THE DRAWINGS

(FIG. 2A) mouse H-2Kb (MHC class I) expression. (FIG. 2B) mouse H-2Db (MHC class I) expression, (FIG. 2C) mouse PD-L1 expression, and (FIG. 2D) D2C7-IT target antigen mEGFRvIII expression on CT-2A-mD2C7 cells.

FIG. 3 In vitro cytotoxicity of D2C7-IT on CT-2A-mD2C7 cells. WST1 assay was utilized to determine the in vitro cytotoxicity of D2C7-IT on CT-2A-mD2C7 cells. The $IC_{50}$ of D2C7-IT on CT-2A-mD2C7 cells was 0.47 ng/ml (lower line) compared to that of the negative control immunotoxin, P588-IT (upper line. $IC_{50}$>1000 ng/ml).

FIG. 4. Survival of C57BL/6 mice injected intracranially with CT2A-mD2C7 cells.

FIG. 5A control brain and FIG. 5B CT2A-mD2C7 tumors. (F480lo+F480int+F480hi)=macrophages FIG. 6. Experimental outline for D2C7-IT. BLZ945 combination therapy.

FIG. 8A shows all the treatment groups followed up to Day 35. FIG. 8B shows treatment groups G4-6 followed up to Day 62 after initial tumor inoculation. Note that 4 out of 10 and 5 out of 10 mice were cured only in treatment groups G5 and G6, respectively.

FIGS. 9A-9B. Tumor rechallenging studies for the cured mice in the combinational treatment groups (G5 and G6). FIG. 9A. Cured mice were first rechallenged with $10^6$ CT2A parental cells on the left flank on Day 72. FIG. 9B shows subsequent challenge with $3 \times 10^5$ CT2A-mD2C7 cells in the brain on Day 126 after the initial CT2A-mD2C7 cell inoculation on the right flank. Tumors grew in all naïve mice (G0), whereas no tumor grew in those cured mice (G5 and G6).

FIG. 10A shows the tumor growth curve for the right (treated) tumors, which was similar to the previous one-side model. FIG. 10B shows the tumor growth curve for the left (untreated) tumors, which showed that the combinational therapy on the right side could also have an antitumor effect on the distant left tumor.

FIG. 11A. On Day 35, compared to treatment group G1, the left tumor growth was significantly delayed in all the other treatment groups, p<0.05 for treatment groups G2. G3, and G4; p<0.01 for treatment groups G5 and G6. FIG. 11B. On Day 43, the left tumor growth was significantly delayed by the combinational therapy compared to the D2C7-IT monotherapy on the right tumor, p<0.05.

DETAILED DESCRIPTION OF THE INVENTION

Figure 1:
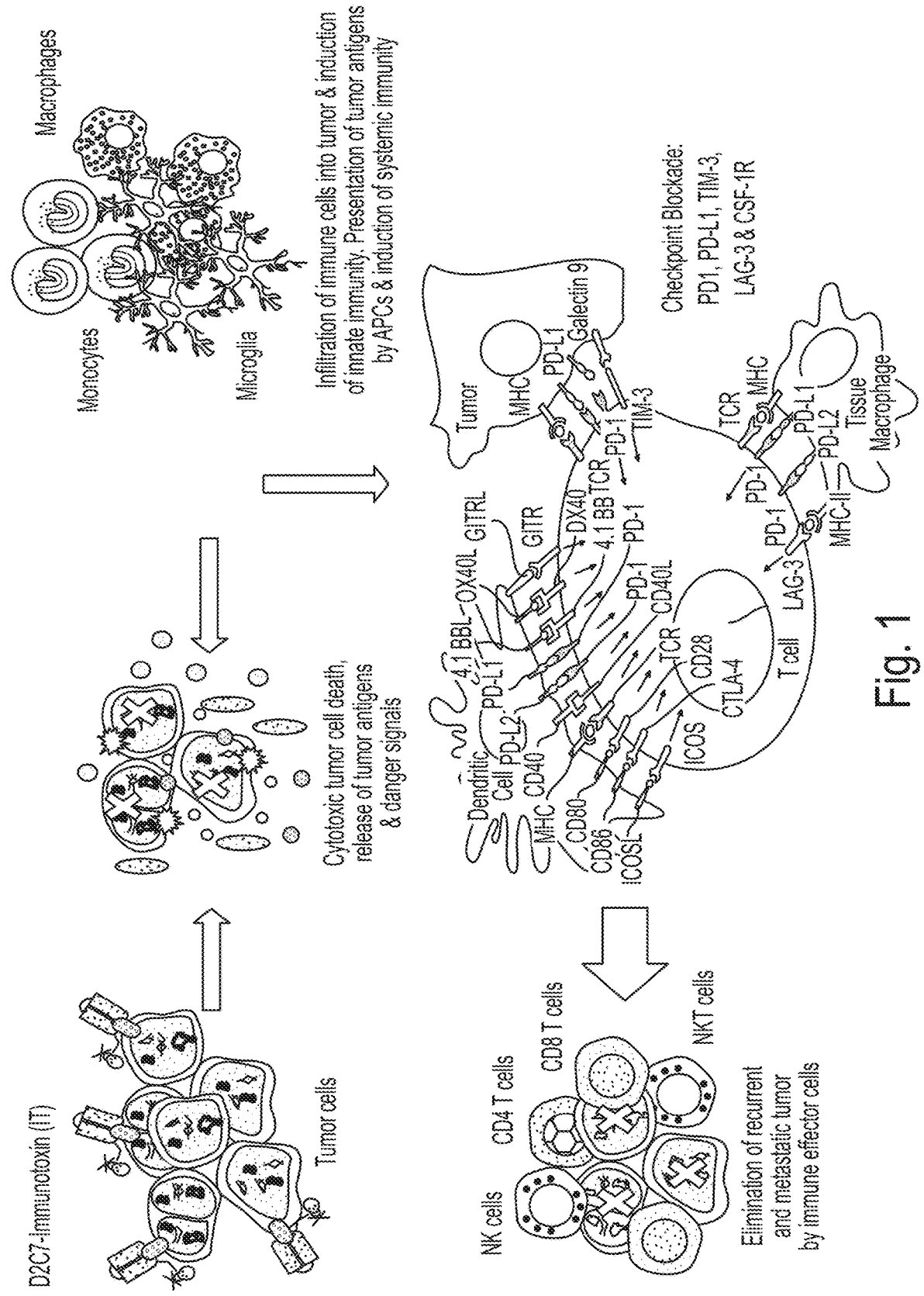
FIG. 1. Possible mechanism for combination of regional cytotoxic therapy and immune checkpoint blockade. Cytotoxic therapy may engender targeted destruction of primary tumors and an 'in situ vaccine' effect. Simultaneous blockade of immune checkpoint receptors PD1. PD-L1, TIM-3, LAG-3, and/or CSF-1R may augment the vaccine-mediated immunity. APCs: Antigen Presenting Cells; PD1: Programmed Death molecule 1; PD-L1: Programmed Death-Ligand 1; TIM-3: T cell Immunoglobulin and Mucin domain-3; LAG-3: Lymphocyte Activation Gene-3; CSF-1R: Colony Stimulating Factor 1 Receptor; NK/NKT: natural killer/natural killer T cells.

The inventors have developed targeted immunotoxins (IT), D2C7-(scdsFv)-PE38KDEL (D2C7-IT), by fusing the single chain variable fragment (scFv) from the D2C7 monoclonal antibody (mAb) with the *Pseudomonas* exotoxin A (PE), optionally fused to KDEL peptide. D2C7-IT reacts with both the wild-type epidermal growth factor receptor (EGFRwt) and the EGFR variant II (EGFRvIII), two proteins that are overexpressed in glioblastoma. The robust antitumor efficacy of D2C7-IT is mediated through PE in orthatopic glioma xenograft models in immunocompromised mice. In addition to direct tumor cell killing, the immunotoxin monotherapy induces a secondary antitumor immune response through the engagement of T cells. When the immunotoxin is administered in a combination regimen with an immune checkpoint inhibitor, improved and synergistic results are observed.

Other moieties which can be attached to the antibodies include those which provide additional beneficial properties. For example, a KDEL (lys-asp-glu-leu) tetra-peptide can be added at the carboxy-terminus of the protein to provide retention in the endoplasmic reticulum. Variants such as DKEL, RDEL, and KNEL which function similarly can also be used.

Tumors which can be treated are any that react with the D2C7 antibody. These include but are not limited to those in which at least one EGFRvIII allele is present. These may be found in breast, head and neck, brain, glioblastoma multiforme, astrocytoma, lung, or other tumors. It may be desirable to determine the presence of such an allele prior to therapy. This can be done using an oligonucleotide-based technique, such as PCR, or using an immunological technique, such as immunohistochemistry. It may be desirable to determine the amount, fraction, ratio, or percentage of cells in the tumor which express EGFR and/or EGFRvIII. The more cells which express EGFR on their surfaces, the more beneficial such antibody therapy is likely to be. Even tumors that express little to no EGFRvIII may be treated due to the ability of the antibody to bind to wild-type EGFR. Optionally, tumors may be tested prior to treatment for reactivity with D2C7 antibody. The immunotoxin itself could be used as an immunohistochemistry agent, before treatment, during treatment, or after treatment. A secondary reagent could be used with the immunotoxin for detection. It could, for example, recognize the *Pseudomonas* component of the immunotoxin.

Immunotoxins can be administered by any technique known in the art. Compartmental delivery may be desirable to avoid cytotoxicity for normal tissues that express EGFR. Suitable compartmental delivery methods include, but are not limited to delivery to the brain, delivery to a surgically created tumor resection cavity, delivery to a natural tumor cyst, and delivery to tumor parenchyma.

Tumors which can be treated by the method of the present invention are any which express epidermal growth factor receptor (EGFR), whether wild type. EGFRvIII, or other variants. Preferably the tumor expresses the receptor in amounts far exceeding expression by normal tissues. The mechanism of high level expression may be by genetic amplification, other alterations, whether genetic or epigenetic or post translational modifications. Exemplary tumors which can be treated include without limitation: malignant gliomas, breast cancer, head and neck squamous cell carcinoma, lung cancer.

Blockade of T cell immune checkpoint receptors, can be performed against any such targets, including but not limited to PD-1, PD-L1, TIM-3, LAG-3. CTLA-4, and CSF-1R and combinations of such checkpoint inhibitors. The immune checkpoint receptors may be on tumor cells or immune cells such as T cells, monocytes, microglia, and macrophages, without limitation. The agents which assert immune checkpoint blockade may be small chemical entities or polymers, antibodies, antibody fragments, single chain antibodies or other antibody constructs, including but not limited to bispecific antibodies and diabodies.

Immune checkpoint inhibitors which may be used according to the invention include any that disrupt the inhibitory interaction of cytotoxic T cells and tumor cells. These include but are not limited to anti-PD-1 antibody, anti-PD-L1 antibody, anti-CTLA4 antibody, anti-LAG-3 antibody, anti-TIM-3 antibody. The inhibitor need not be an antibody, but can be a small molecule or other polymer. If the inhibitor is an antibody it can be a polyclonal, monoclonal, fragment, single chain, or other antibody variant construct. Inhibitors may target any immune checkpoint known in the art, including but not limited to, CTLA-4, PDL1, PDL2, PD1, B7-H3, B7-H4, BTLA, HVEM, TIM3, GAL9, LAG3, CSF-1R, VISTA, KIR, 2B4, CD160, CGEN-15049, CHK 1, CHK2, IDO, A2aR, and the B-7 family of ligands. Combinations of inhibitors for a single target immune checkpoint or different inhibitors for different immune checkpoints may be used.

Examples of inhibitors of CSF-1R which may be used in the combination therapy with the immunotoxin include, without limitation, the following agents which are in clinical development: PLX3397. PLX486, RG7155, AMG820, ARRY-382, FPA008, IMC-CS4, JNJ-40346527, and MCS 110.

The immune checkpoint inhibitor may be administered at the same time, before, or after the immunotoxin. Typically the two agents will be administered within 30, 28, 21, 14, 7, 4, 2, or 1 day(s) of each other. The agents may be given repeatedly, either serially or in a cycle of first and second agents. It may be advantageous but not necessary for the vaccine to be administered prior to the checkpoint inhibitor. But the reverse order may also be used. Priming of a cytotoxic T lymphocyte response by the immunotoxin may take from about 5 to about 14 days. Administration of the checkpoint inhibitor may beneficially be commenced during or after the priming period.

Immune checkpoint inhibitors may be administered by any appropriate means known in the art for the particular inhibitor. These include intravenous, oral, intraperitoneal, sublingual, intrathecal, intracavitary, intramuscularly, and subcutaneously.

Treatment regimens may include, in addition to delivery of the immunotoxin and immune checkpoint inhibitor(s), surgical removal of the tumor, surgical reduction of the tumor, chemotherapy, biological therapy, radiotherapy. These modalities are standard of care in many disease states, and the patient need not be denied the standard of care. The immunotoxin and immune checkpoint inhibitor(s) may be administered before, during, or after the standard of care. The immunotoxin and immune checkpoint inhibitor(s) may be administered after failure of the standard of care.

Kits may comprise, in a single divided or undivided container, the immunotoxin or its components or its encoding DNA and the immune checkpoint inhibitor or combination of immune checkpoint inhibitors. Storage stability may vary between the two agents so separate vessels may be used. Optionally one or both agents may be lyophilized or frozen.

Immunotoxins can directly kill cancer cells that express high levels of the targeted tumor antigen. Immunotoxin monotherapy can efficiently and directly destroy tumor cells expressing targeted epitopes, such as EGFRwt and/or its truncated variant, EGFRvIII, in malignant brain tumor xenograft models in immunocompromised mice. Immunotoxin therapy can induce a secondary anti-tumor immune response in a mouse model, which is different from the direct killing mechanism and needs the cooperation of the immune system. Since malignant brain tumors are always a heterogeneous mass, it is possible that some tumor cells can escape from the direct targeted attack of the immunotoxin therapy due to the lack of epitopes. For this reason, the secondary anti-tumor immune response stimulated by the immunotoxin may play an important role in eliminating those tumor cells not directly targeted.

Recently, several studies successfully demonstrated that tumor regression and significantly improved survival were achieved in murine glioma models by suppressing co-inhibitory molecules, such as CTLA4, CSF-1R. IDO, and PD1. Based on the promising preclinical data, several clinical trials have started to investigate the utilization of immune checkpoint inhibitors to treat malignant brain tumors, either as monotherapy or combinatorial therapy with other anti-tumor agents.

However, malignant gliomas, including glioblastomas, have relatively low mutation rates, which may generate fewer and subtle tumor antigens, leading to relatively poor basal immunogenicity compared to other tumor types that respond well to immunotherapies, for example, melanoma and NSCLC. Therefore, a combination of targeted cytotoxic immunotherapy and immune checkpoint inhibitors may provide a synergistic anti-tumor effect.

The ideal combinatorial therapy may have a lower dose of targeted cytotoxic immunotherapy to limit its side effects, and achieve long-term anti-tumor immunity. Immunotoxin therapy can efficiently and directly kill cancer cells that express high levels of the targeted antigen through its unique cytotoxic mechanism. Cancer cells destroyed by localized immunotoxin therapy release tumor antigens and/or other neoantigens. These antigens can then be presented by the APCs to host T cells in the local draining lymph nodes, which activate CTLs to migrate and eliminate the remaining or recurrent tumor cells expressing specific tumor antigens at the tumor site. Throughout this process, various co-inhibitory checkpoint pathways between T cells and APCs and/or between T cells and tumor cells can trigger different mechanisms to de-activate T cells, and to adjust the continuation and intensity of the anti-tumor immunity. Immune checkpoint inhibitors, such as anti-CTLA4 and anti-PD1 mAbs, can block these immunosuppressive pathways and therefore augment tumor cell death caused by lymphocytes activated by the targeted immunotoxin therapy.

Figures 8A, 8B:
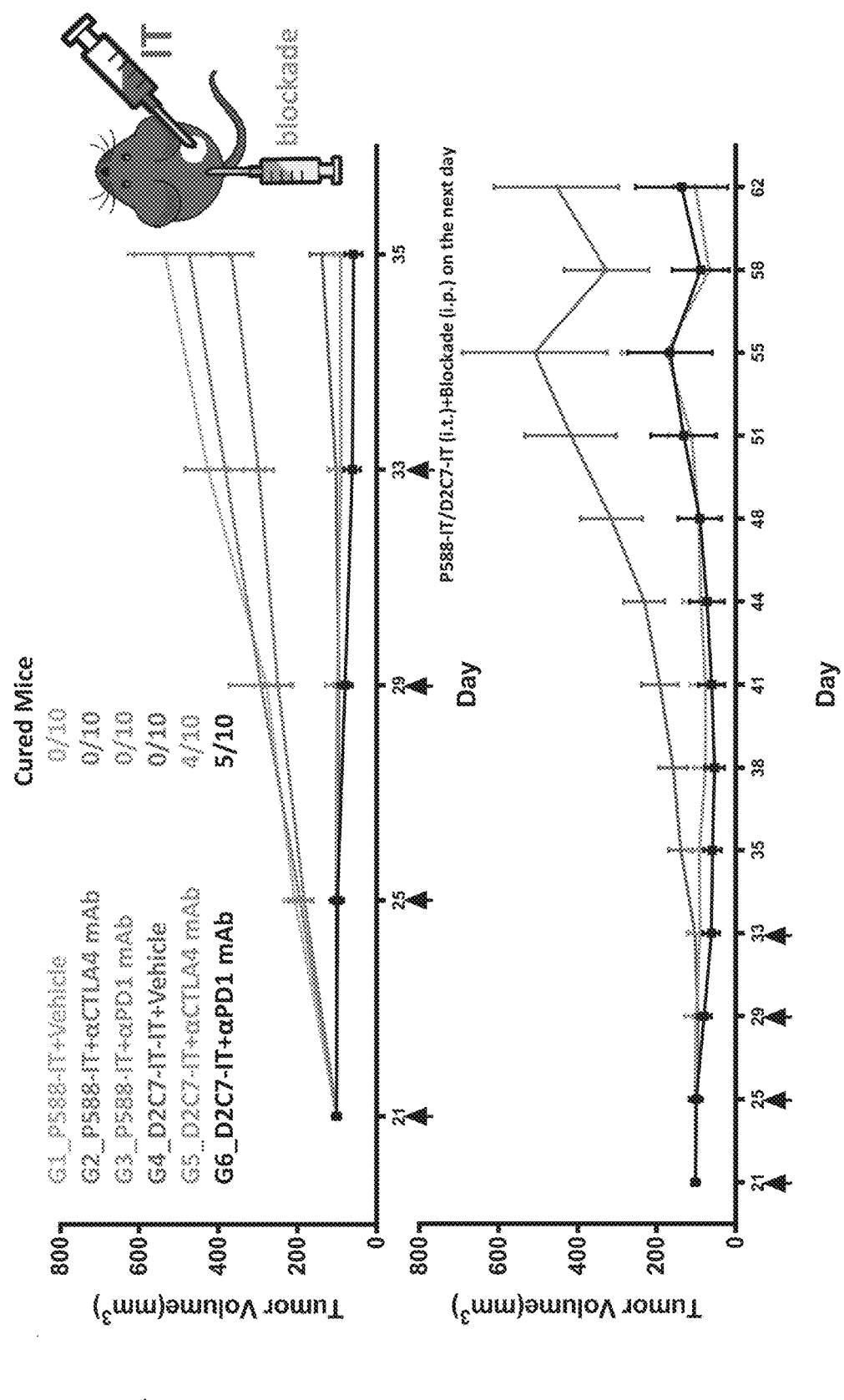
FIGS. 8A-8B. In vivo efficacy of D2C7-IT+ (αCTLA-4 or αPD-1) mAb combination therapy in subcutaneous CT2A-mD2C7 glioma-bearing C57BL/6 immunocompetent mice.

We established a subcutaneous mouse CT2A-mD2C7 glioma model in C57BL/6 immunocompetent mice with six groups, in which the mice were treated by the control immunotoxin P588-IT or D2C7-IT, combined with αCTLA4 or αPD1 inhibitors after the tumor grew to a certain size. In this in vivo subcutaneous CT2A-mD2C7 glioma model, four doses of the low-dose D2C7-IT but not αCTLA4 or αPD1 monotherapy, and D2C7-IT+αCTLA-4 or αPD-1 combinatorial therapy generated a significant delay in tumor growth compared to the control immunotoxin P588-IT treatment groups (FIGS. 8A and 8B). Importantly, complete cures were only observed in D2C7-IT+αCTLA4 (n=4/10) and D2C7-IT+αPD-1 (n=5/10) combinatorial therapy groups (FIGS. 8A and 8B), although D2C7-IT monotherapy could also significantly delay the tumor growth. These results demonstrated that low doses of cytotoxic immunotoxin therapy can significantly delay the tumor growth but fail to cure the tumor-bearing mice. Combined with immune checkpoint inhibitors, cytotoxic immunotoxin therapy can increase the initial cure rate of low-dose immunotoxin therapy from zero to over 40%. Furthermore, all cured mice rejected the mD2C7-negative tumors primary subcutaneous rechallenge, whereas tumors grew in untreated naïve mice, suggesting that the combinatorial treatment provided long lasting anti-tumor immunity that even extended to mD2C7-negative parental cells, as well (FIG. 9A). All nine cured mice then rejected the CT2A-mD2C7 secondary intracranial rechallenge in the brain, whereas tumors grew in untreated naïve mice, indicating that the combinatorial treatment also provided long lasting anti-tumor immunity that extended to the remote immune-privileged CNS as well (FIG. 9B), in which the central memory T cells ($T_{CM}$) might play an important role.

Figures 10A, 10B:
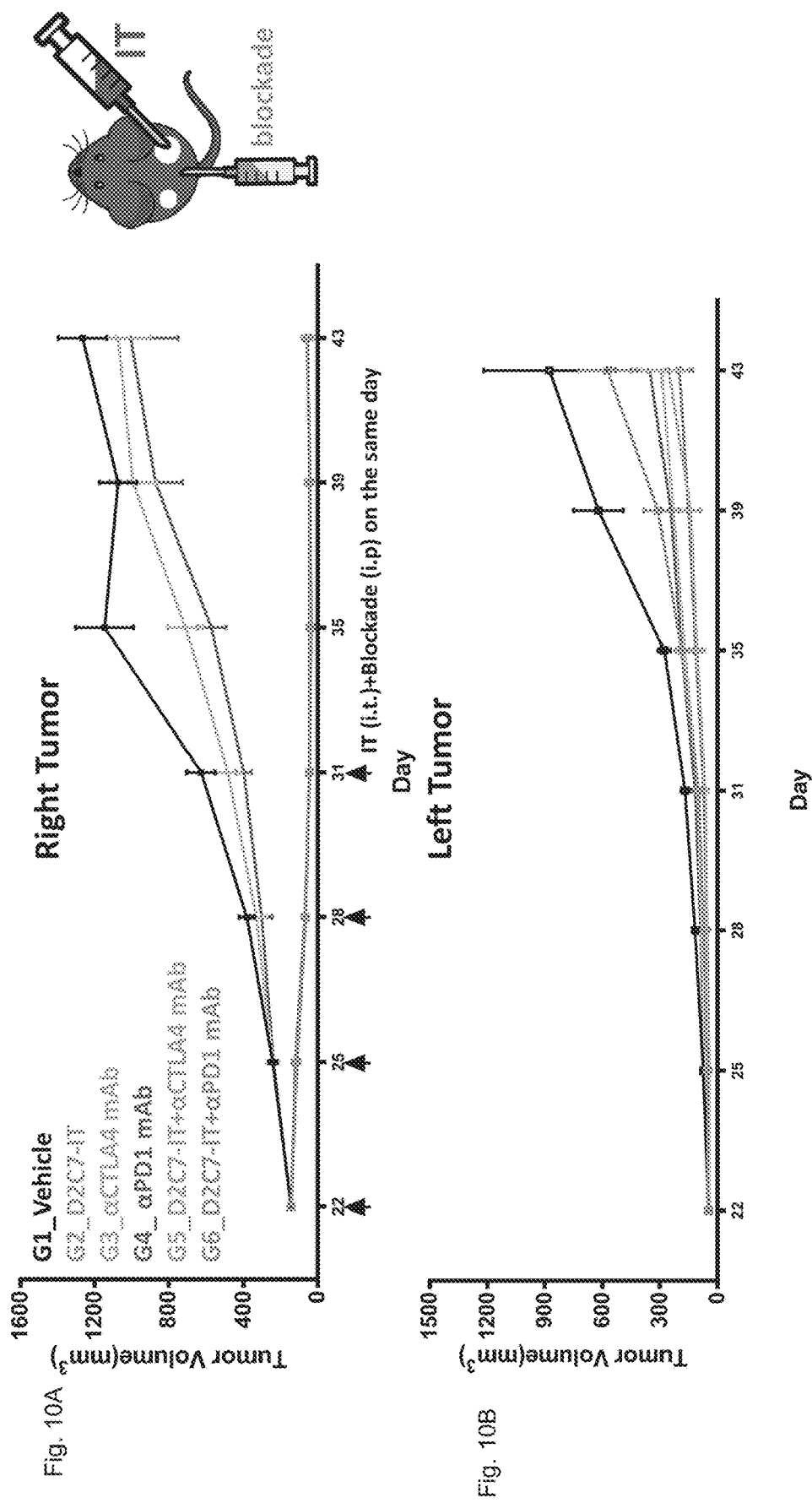
FIGS. 10A-10B. In vivo efficacy of D2C7-IT+(αCTLA-4 or αPD-1) mAb combination therapy in bilateral subcutaneous CT2A-mD2C7 glioma-bearing C57BL/6 immunocompetent mice.
Figures 11A, 11B:
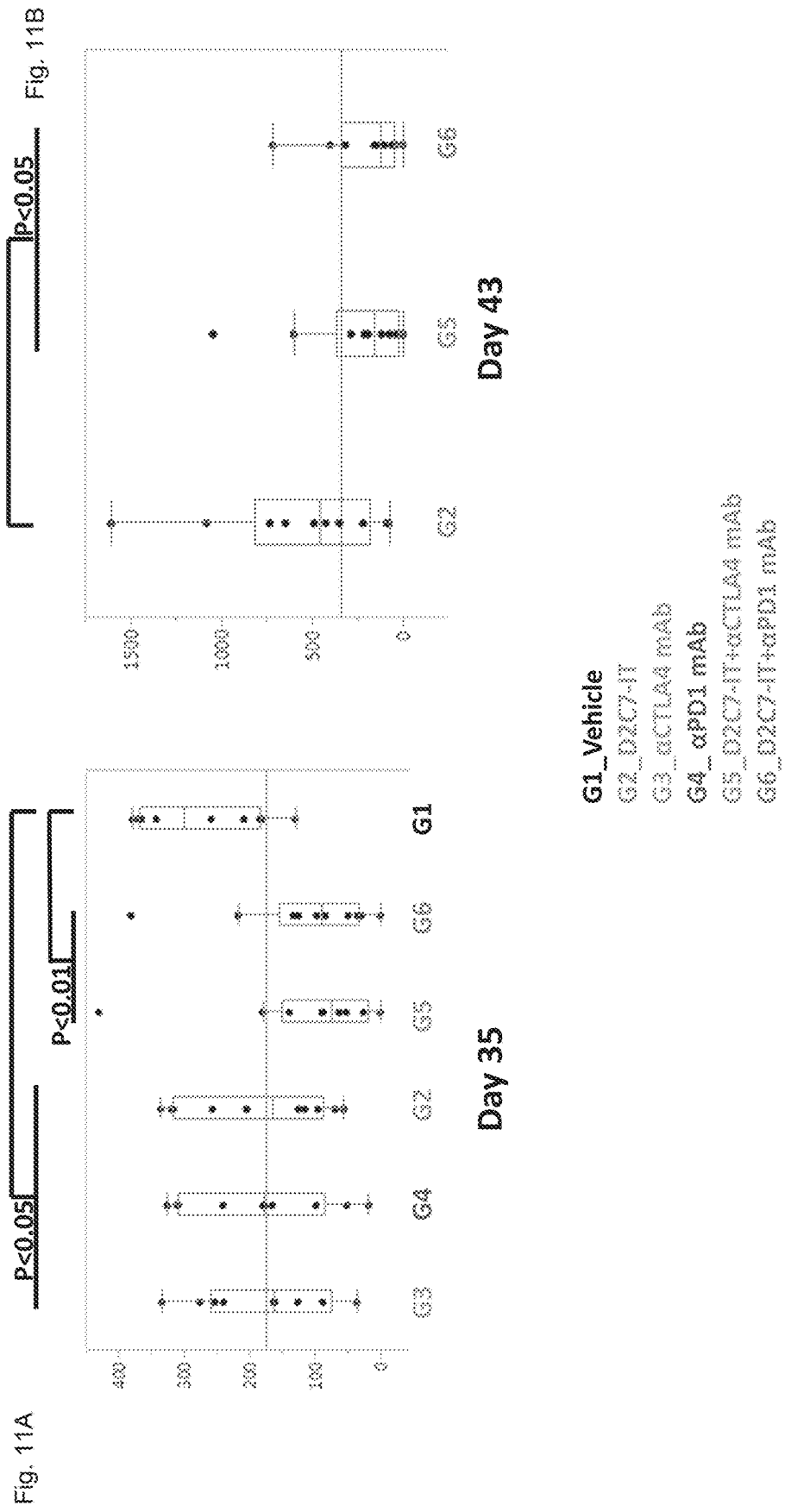
FIGS. 11A-11B. Left tumor volume among groups on Day 35 and Day 43 after the initial tumor inoculation.

Subsequently, we established a bilateral subcutaneous mouse glioma model to investigate whether a localized high-dose immunotoxin treatment can provide a systemic anti-tumor effect on the tumors in the distal region, and whether the combination of immune checkpoint inhibitors can enhance this systemic anti-tumor immunity induced by the localized immunotoxin therapy. The D2C7-IT monotherapy. D2C7-IT+αCTLA4, and D2C7-IT+αPD1 combinatorial therapy led to significant growth delay of the right tumors (P<0.01), and cured 4/10, 6/10, and 5/10 right tumors, respectively (FIG. 10A). Interestingly, in the groups where the right tumors were treated by D2C7-IT or αCTLA-4 or αPD-1 monotherapy or D2C7-IT+(αCTLA-4 or αPD-1) combinatorial therapy, the left untreated tumors also grew much slower compared to the control group (FIGS. 10B and 11A), which indicates that a high dose of localized D2C7-IT monotherapy can achieve a similar anti-tumor immunity on the left untreated tumors compared to the systemic immune checkpoint inhibitor monotherapy. Furthermore, the combination therapy in the right tumors led to the most significantly delayed growth of the left untreated tumors in the mice (FIGS. 10B and 11B), which suggests that immune checkpoint inhibitors can enhance the anti-tumor immunity induced by the localized immunotoxin therapy to restrict the tumor growth in the remote area.

We have demonstrated that the intratumoral delivery of D2C7-IT induces secondary anti-tumor immunity, which destroys not only mD2C7-expressing tumor cells, but also tumor cells not expressing mD2C7 at the systemic level. A combination of D2C7 immunotoxin with immune checkpoint inhibitors can enhance this immunotoxin-induced anti-tumor immunity to achieve a synergistic long-term anti-tumor effect.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

We established a mouse glioma line, CT-2A-mD2C7, overexpressing the D2C7-IT antigen mouse EGFRvIII (mEGFRvIII). The reactivity and therapeutic efficacy of D2C7-IT against CT-2A-mD2C7 cells was determined by flow cytometry and in vitro cytotoxicity assays (WST1), respectively. CT-2A-mD2C7 cells were further analyzed for MHC class I and PD-L1 expression by flow cytometry. In vivo efficacy of D2C7-IT or αCTLA-4 or αPD-1 monotherapy or D2C7-IT+αCTLA-4 or D2C7-IT+αPD-1 combination therapy was evaluated in subcutaneous CT-2A-mD2C7 glioma-bearing C57BL/6 immunocompetent mice.

WST-1 is a reagent for measuring cell proliferation. It is used for the nonradioactive, spectrophotometric quantification of cell proliferation and viability in cell populations. The assay is based on the cleavage of the tetrazolium salt WST-1 to formazan by cellular mitochondrial dehydrogenases. Expansion in the number of viable cells results in an increase in the activity of the mitochondrial dehydrogenases, which in turn leads to increase in the amount of formazan dye formed. The formazan dye produced by viable cells can be quantified by measuring the absorbance at L=440 nm.

Example 2

Figure 2A:
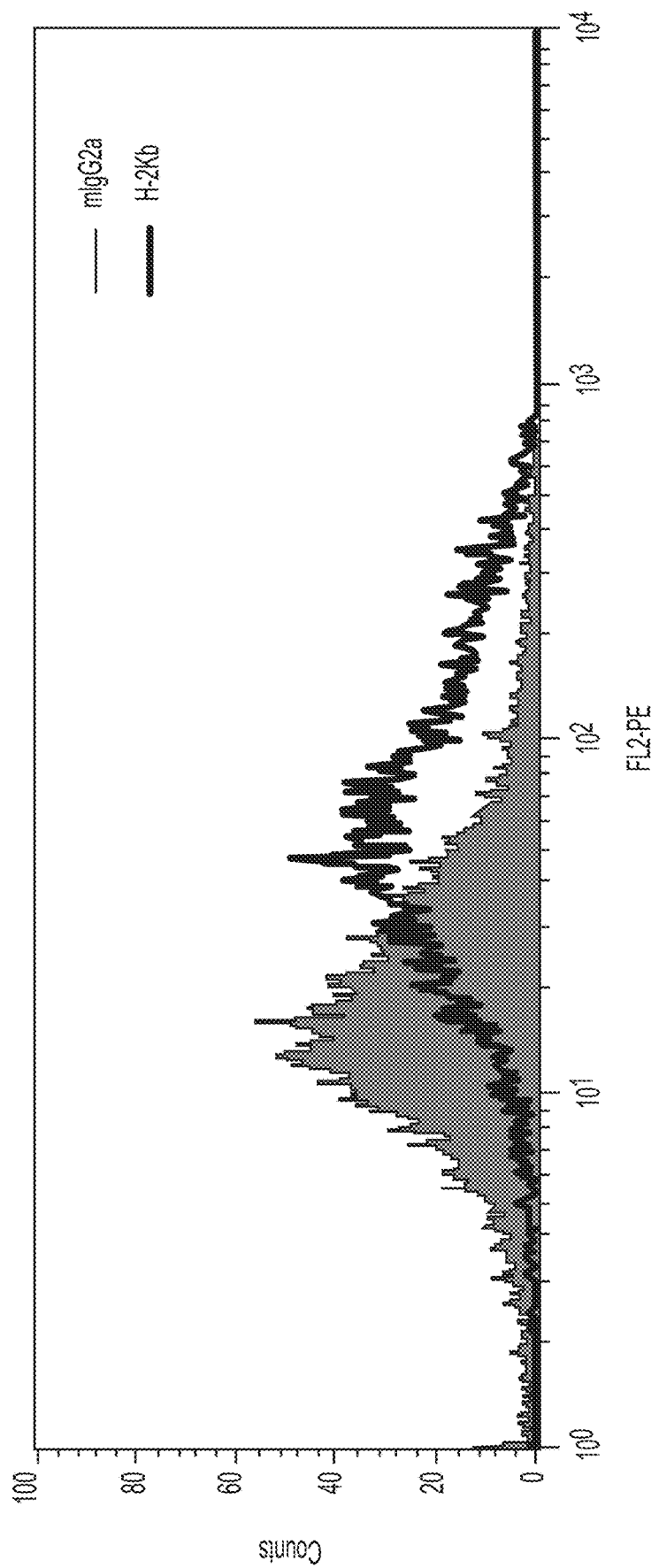
FIGS. 2A-2D Flow cytometry analyses of the CT-2A-mD2C7 cell line.
Figure 2B:
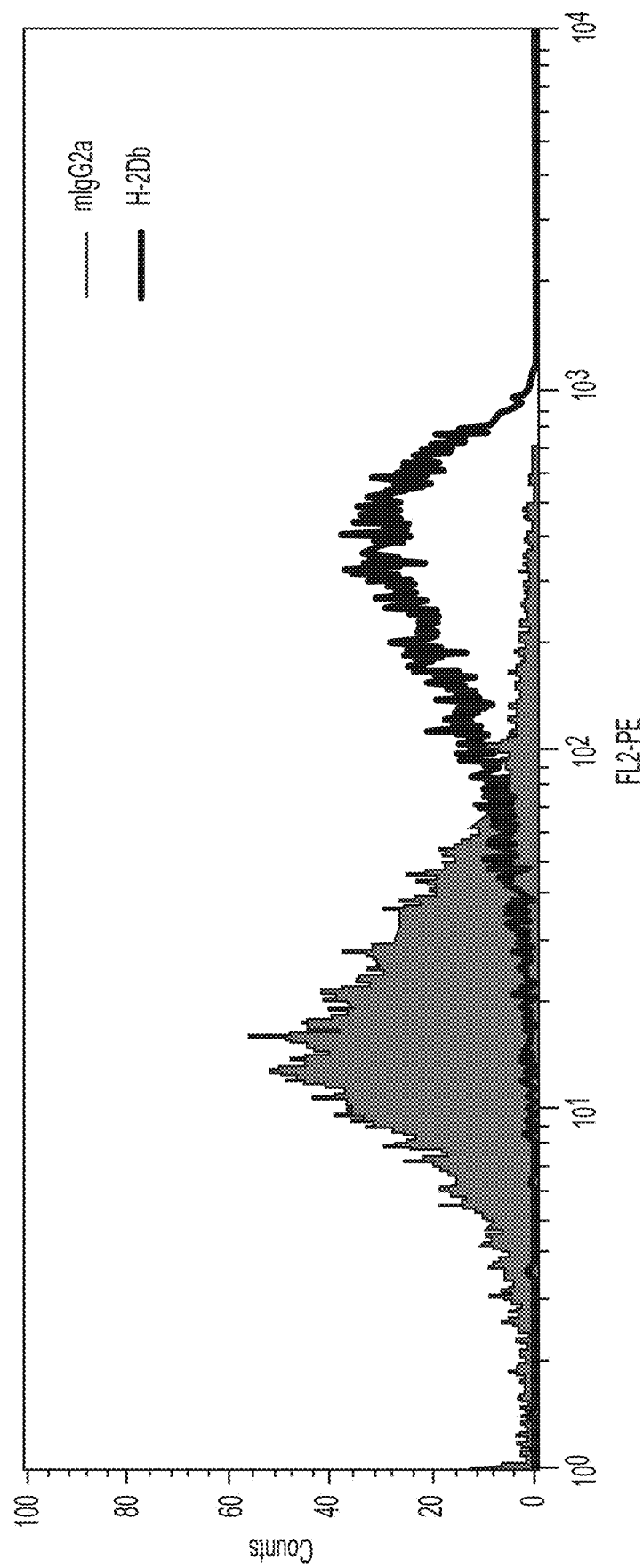
Figure 2D:
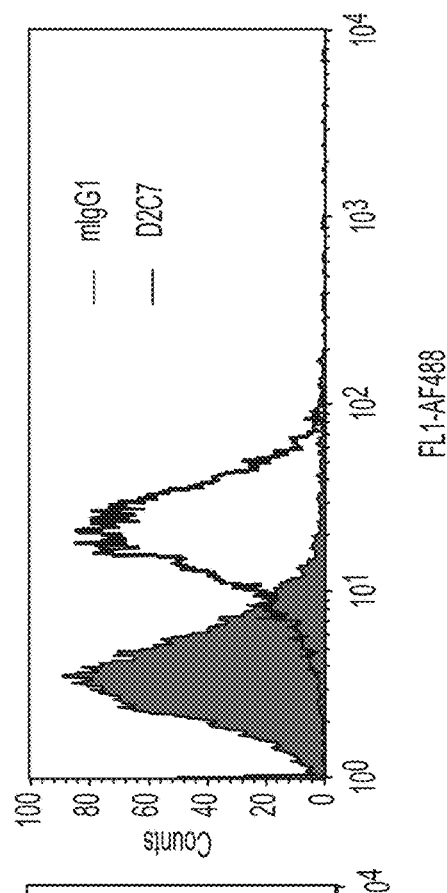
Figure 2C:
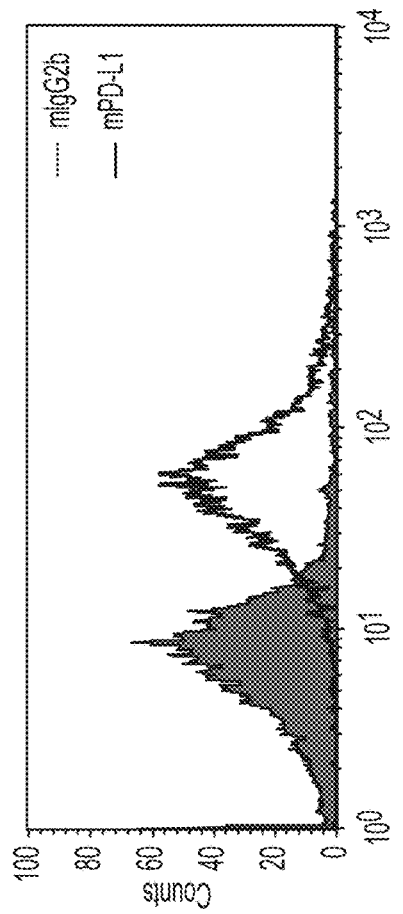
Figure 3:
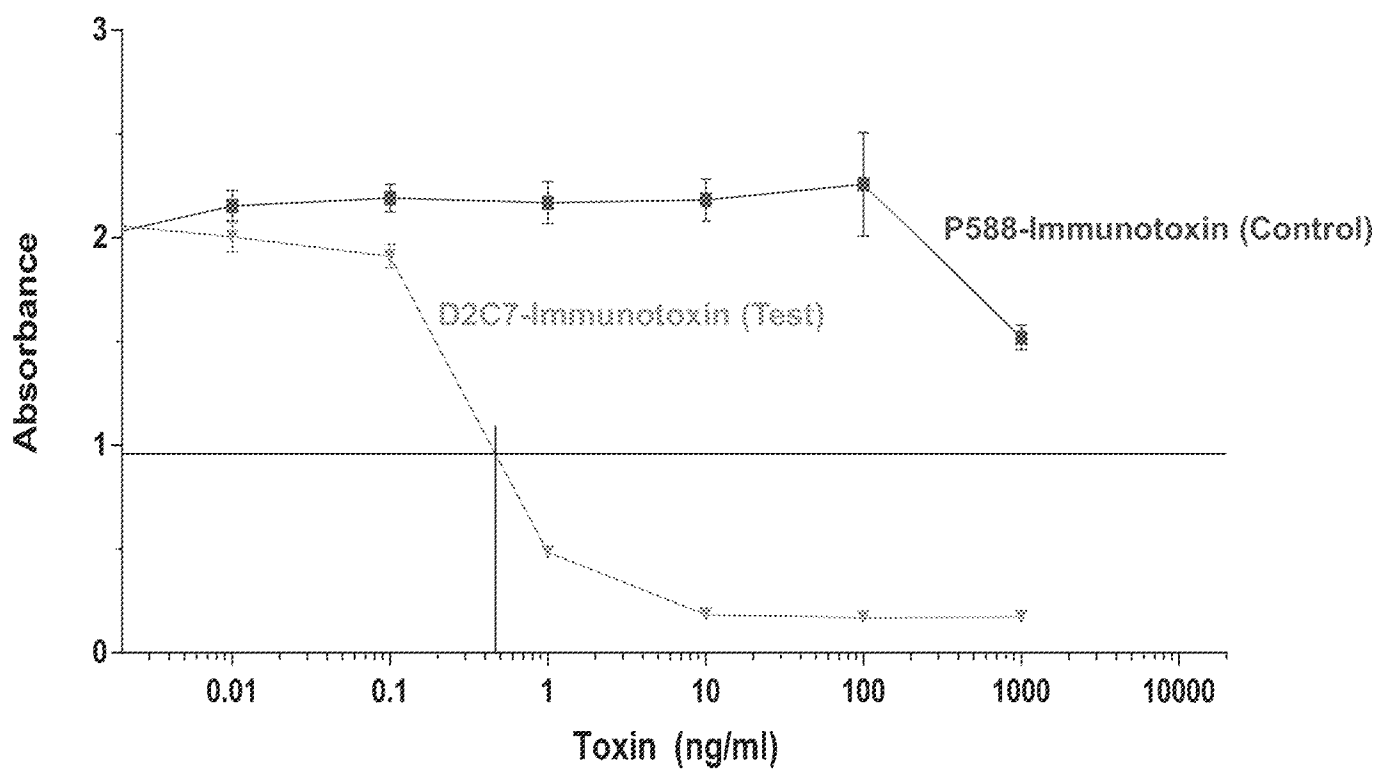

Flow cytometry analysis confirmed the specific binding ability of D2C7 monoclonal antibody to the CT-2A-mD2C7 cells (FIG. 2D). Flow cytometry also demonstrated a high expression of both MHC class I molecules (FIGS. 2A and 2B) and PD-L (FIG. 2C) on tumor cell surface. D2C7-IT was highly cytotoxic (IC50=0.47 ng/mL) against CT-2A-mD2C7 cells in in vitro WST1 cytotoxicity assay (FIG. 3).

Example 3

Construction, expression, and purification of D2C7-(scdsFv)-PE38KDEL immunotoxin. The carboxyl terminus of the D2C7 $V_H$ domain was connected to the amino terminus of the $V_L$ domain by a 15-amino-acid peptide (Gly$_4$Ser)$_3$ linker. In order to obtain a stable IT, it is essential to ensure that during renaturation $V_H$ is positioned near $V_L$. This was achieved by mutating a single key residue in each chain to cysteine, for the stabilizing disulfide bond to form. On the basis of predictions using molecular modeling and empirical data with other dsFv-recombinant ITs, we chose one amino acid in each chain to mutate to cysteine. These are residues 44 in the framework region 2 (FR2) of $V_1$ and 100 in the FR4 of $V_L$ (according to the Kabat numbering). Thus, we prepared an Fv that contains both a peptide linker and a disulfide bond generated by cysteine residues that replace Ser44 of $V_H$ and Gly100 of $V_L$. The D2C7 (scdsFv) PCR fragment was then fused to DNA for domains II and III of *Pseudomonas* exotoxin A. The version of *Pseudomonas* exotoxin A used here, PE38KDEL, has a modified C terminus which increases its intracellular retention, in turn enhancing its cytotoxicity. The D2C7-(scdsFv)-PE38KDEL was expressed in *E. coli* under the control of T7 promoter and harvested as inclusion bodies.

Example 4

Targeting Tumor and Tumor-Associated Macrophages for Glioblastoma Therapy:

We evaluated the ability of D2C7-IT and BLZ945 combination treatment to function synergistically and produce an effective antitumor response in immunocompetent glioblastoma mouse models.

Intracranial Growth Curve for CT2A-mD2C7 in C57BL/6 Mice:

To determine the time course of CT2A-mD2C7 intracranial tumor growth, 3×10$^5$ cells/3 μl were implanted into 9 female C57BL/6 mice, and a survival curve was plotted (FIG. 4). The CT2A-mD2C7 survival curve demonstrated that 100% death occurred at day 25 post-tumor implantation. Based on our previous studies, post-tumor implantation day 8 was chosen as the optimal day to initiate D2C7-IT infusion.

Figure 5A:
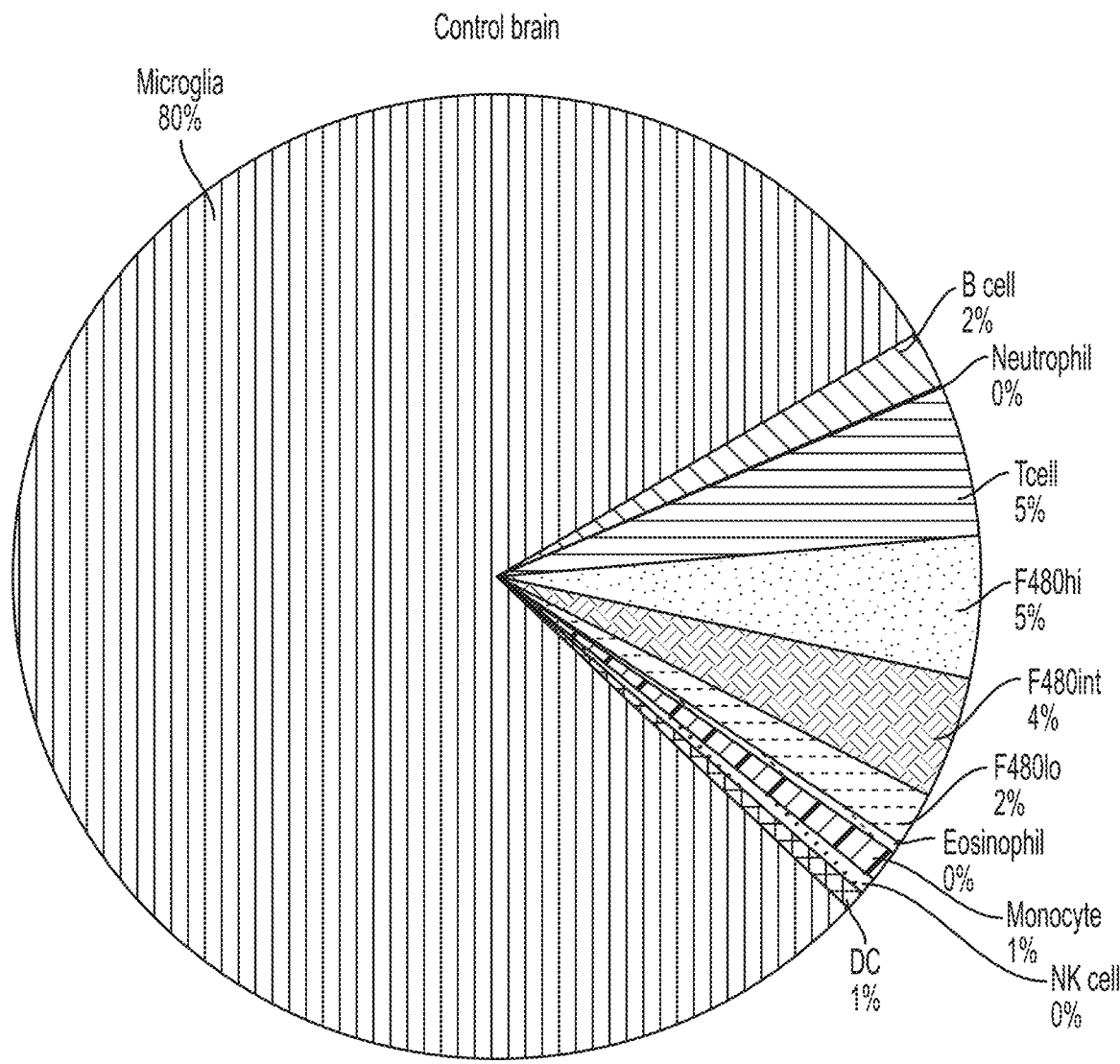
FIGS. 5A-5B. Phenotypic profile of the immune cells populating the CT2A-mD2C7 brain tumor microenvironment.
Figure 5B:
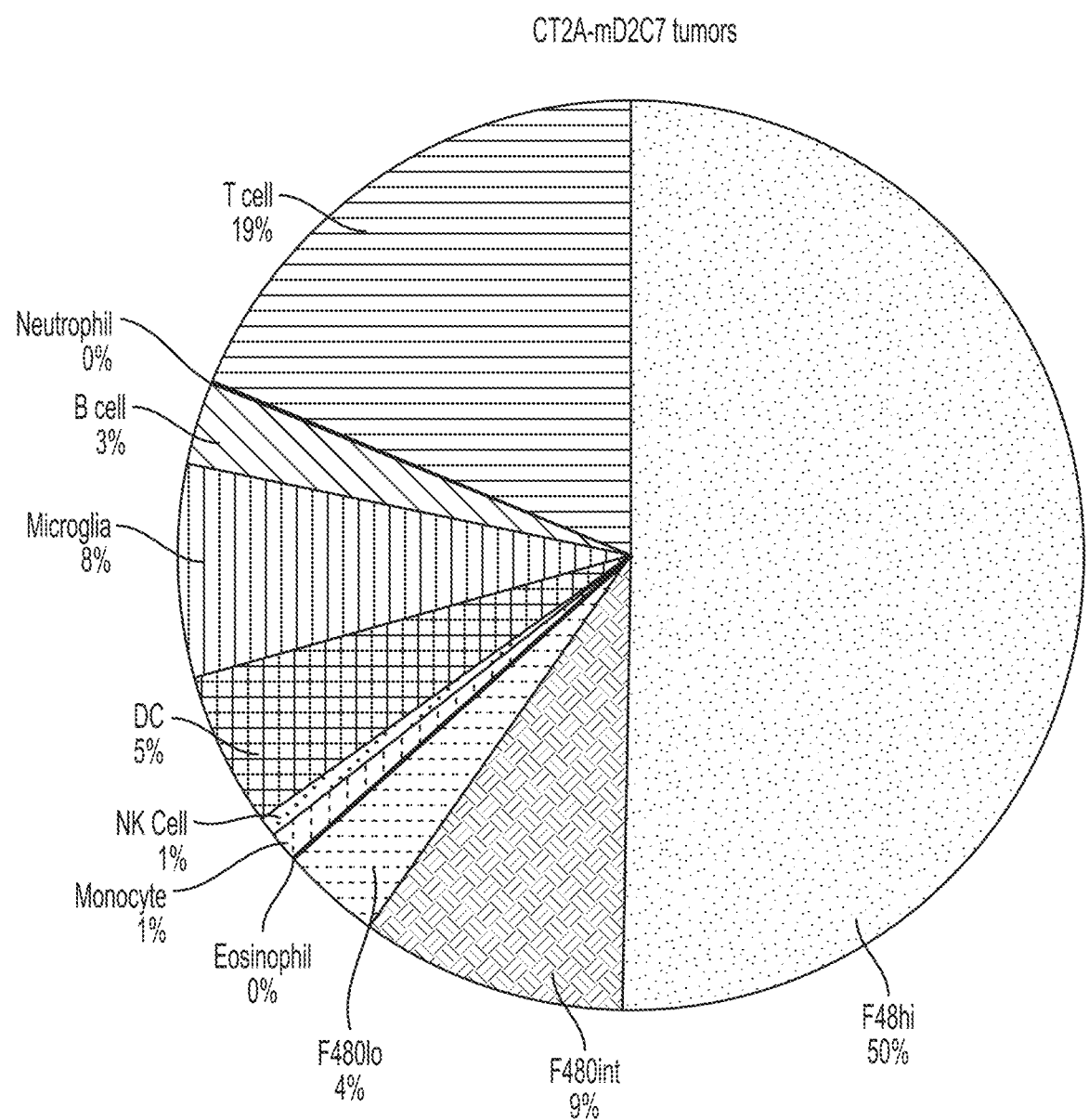

Phenotypic Profile of the Immune Cells Populating the CT2A-mD2C7 Brain Tumor Microenvironment:

To characterize the immune cell phenotype of intracranial CT2A-mD2C7 tumors, C57BL/6 immunocompetent mice were implanted with 3×10$^5$ tumor cells. The mice were followed to assess tumor development and were euthanized when they became moribund. Upon euthanization, the brains were harvested and the tumors were analyzed for infiltrating immune cells by flow cytometry. Cells isolated from naïve C57BL/6 mice were used as the control. The primary cell types in the normal brain were microglia (80%), macrophages (F480Io+F480int+F480hi=11%), and T cells (5%) (FIG. 5A). However, there was a significant change in the percentage of microglia (8%), macrophages (F480Io+F480int+F480hi=63%), and T cells (19%) in tumor-bearing mice (FIG. 5B).

Figure 6:
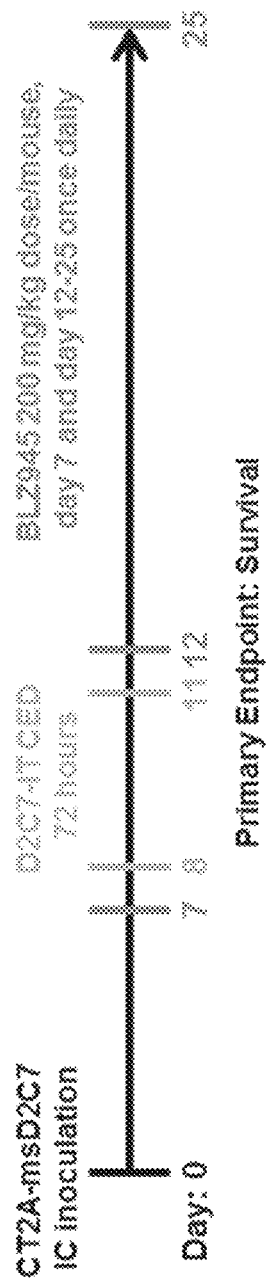
Figure 7:
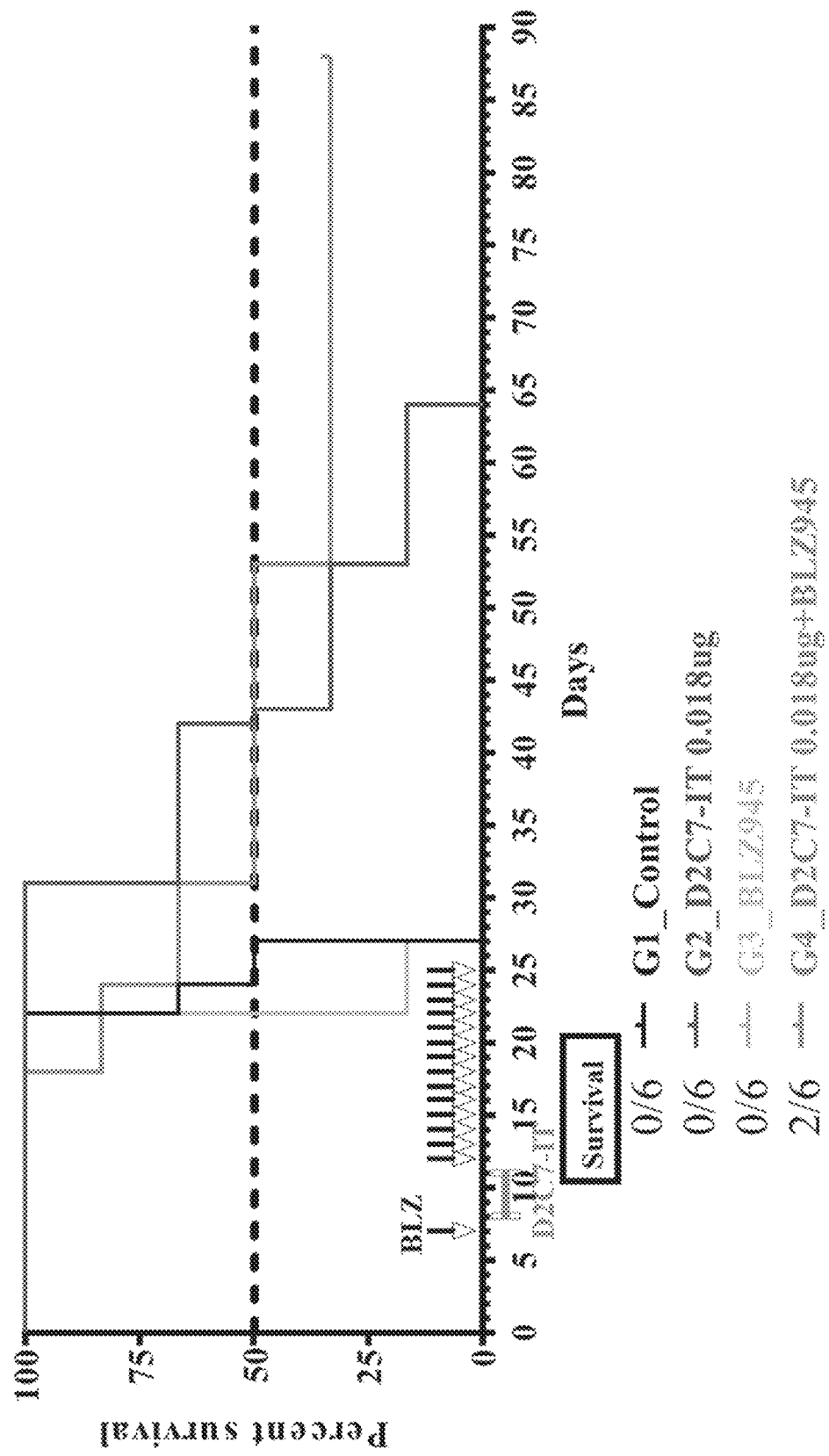
FIG. 7. Anti-tumor efficacy of D2C7-IT and BLZ945 combination therapy against the intracranial CT2A-mD2C7 glioma model.

Anti-Tumor Efficacy of D2C7-IT and BLZ945 Combination Therapy Against the Intracranial CT2A-mD2C7 Glioma Model:

The experimental outline for D2C7-IT+BLZ945 combination therapy against the CT2A-mD2C7 cell line is shown in FIG. 6. The in vivo efficacy of D2C7-IT or BLZ945 monotherapy or D2C7-IT+BLZ945 combination therapy was evaluated in intracranial CT2A-mD2C7 glioma-bearing C57BL/6 immunocompetent mice (FIG. 7). D2C7-IT (0.018 μg total dose) was infused by an osmotic pump via convection-enhanced delivery (CED) for 72 hours from Day 8 to Day 11 post-tumor inoculation. BLZ945 (200 mg/kg) was delivered once daily through oral gavage on day 7 and on days 12-25. The survival curves for mice treated with the vehicle control and with BLZ945 monotherapy looked similar (Median Survival=22-24 days. FIG. 7). At a total dose of 0.018 μg, D2C7-IT monotherapy extended the median survival to 42 days (FIG. 7). The median survival for the D2C7-IT+BLZ945 combination therapy group was 53 days (FIG. 7). Significantly, complete cures were observed only in the combination therapy group (2/6 mice). The preliminary data suggests that glioblastoma patients will benefit from D2C7-IT and BLZ945 combination therapy.

Example 5

In Vivo Efficacy of D2C7-IT+(Anti-CTLA4 or Anti-PD1) Inhibitors Combinatorial Therapy in a Subcutaneous (SC) CT2A-mD2C7 Glioma Model.

In previous pilot studies, we observed that the subcutaneous rechallenged mouse glioma allografts were rejected in those immunocompetent mice bearing SC mouse glioma allografts cured by the intratumoral (i.t.) immunotoxin therapy, suggesting that there can be a memory anti-tumor immune response following the SC immunotoxin therapy. This phenomenon was also reported in the SC melanoma mouse model treated by an immunotoxin targeting IL-13, in which CTLs played a major role in mediating this immunotoxin-induced anti-tumor response, although melanoma is a dramatically different type of tumor compared to malignant gliomas in the CNS. Therefore, it is necessary to establish appropriate mouse glioma models to investigate the secondary immune response, induced by immunotoxins, against glioblastomas, and to determine how to enhance this response by the combinatorial therapy of immune checkpoint inhibitors, such as anti-CTLA4 or anti-PD1 antibodies (αCTLA4 or αPD1), in order to achieve a long-lasting remission.

We established a subcutaneous mouse CT2A-mD2C7 glioma model in C57BL/6 immunocompetent mice with six groups, in which the mice were treated by the control immunotoxin P588-IT or D2C7-IT, combined with αCTLA4 or αPD1 inhibitors. In this in vivo subcutaneous CT2A-mD2C7 glioma model, four doses (every 3 days) of the D2C7-IT (low dose, 1.5 μg per mouse per dose, i.t.) but not αCTLA4 (100 μg per mouse per dose, intraperitoneal [i.p]) or αPD1 (250 μg per mouse per dose, i.p.) monotherapy and D2C7-IT+αCTLA-4 or αPD-1 combinatorial therapy (immune checkpoint inhibitors administered on the next day after IT therapy) generated a significant delay in tumor growth compared to the control immunotoxin P588-IT treatment groups (P<0.01, FIG. 8A). Importantly, complete cures were only observed in D2C7-IT+αCTLA4 (n=4/10) and D2C7-IT+αPD-1 (n=5/10) combinatorial therapy groups (FIGS. 8A and 8B), although D2C7-IT monotherapy could also significantly delay the tumor growth.

Example 6

Tumor Rechallenging Studies on the Cured Mice from the D2C7-IT and Immune Checkpoint Inhibitors Combinatorial Treatment Groups To determine whether those cured mice from D2C7-IT and immune checkpoint inhibitors combinatorial treatment groups can recall a protective anti-tumor memory immune response, on Day 72 after the initial tumor challenge, all nine cured mice were then first subcutaneously rechallenged (1° SCR) with a dose of $10^6$ CT2A parental cells in the left flank. All these mice rejected the mD2C7-negative tumors, whereas tumors grew in all untreated naïve mice, suggesting that the combinatorial treatment provided long lasting anti-tumor immunity that extended to mD2C7-negative parental cells as well (FIG. 9A).

To determine whether this protective anti-tumor immunity can protect the mice from the tumor rechallenging in a remote immune-privileged region, for example, the brain, all nine cured mice were then intracranially (IC) rechallenged (2° ICR) for a second time on Day 126 (after the initial subcutaneous tumor challenge) with a dose of $3\times10^5$ CT2A-mD2C7 cells in the brain. At the end of this study, all surviving mice were euthanized for brain histopathologic examination, which did not show tumors in the brains (data not shown). All these mice rejected the CT2A-mD2C7 intracranial (IC) rechallenge (2° ICR), whereas tumors grew in all untreated naïve mice, suggesting that the combinatorial treatment also provided long lasting anti-tumor immunity that extended to the remote immune-privileged CNS as well (FIG. 9B).

Example 7

In Vivo Efficacy of D2C7-IT+(Anti-CTLA4 or Anti-PD1) Inhibitors Combinatorial Therapy in a Bilateral Subcutaneous CT2A-mD2C7 Glioma Model.

In an in vivo bilateral subcutaneous CT2A-mD2C7 glioma model, tumor cells were inoculated in both sides of the flank simultaneously in C57BL/6 mice, with a high density ($3\times10^6$ cells) on the right side and a low density ($10^6$ cells) on the left side. The larger tumors (on the right) were treated with four doses (every two days) of D2C7-IT or αCTLA4 or αPD1 monotherapy or D2C7-IT+αCTLA4 or D2C7-IT+αPD1 combination therapy (immune checkpoint inhibitors administered on the same day of immunotoxin therapy), while the left tumors were untreated. The D2C7-IT monotherapy (high dose, 4.5 µg per mouse per dose, intratumoral), D2C7-IT+αCTLA4 (100 µg per mouse per dose, intraperitoneal), and D2C7-IT+αPD1 (250 µg per mouse per dose, intraperitoneal.) combinatorial therapies led to significant growth delays of the right tumor (P<0.01), which cured 4/10, 6/10, and 5/10 right tumors, respectively (FIG. 10A).

Interestingly, in the groups where the right tumors were treated with D2C7-IT or αCTLA-4 or αPD-1 monotherapy or D2C7-IT+(αCTLA-4 or αPD-1) combinatorial therapy, the left untreated tumors also grew much slower compared to the control group (FIGS. 10B and 11A), which indicates that a high dose of localized D2C7-IT monotherapy can achieve a similar anti-tumor immunity in the left untreated tumors compared to the systemic immune checkpoint inhibitor monotherapy. Furthermore, the D2C7-IT+(αCTLA-4 or αPD-1) combinatorial therapy in the right tumors led to the most significantly delayed growth of the left untreated tumors in the mice (FIGS. 10B and 11B), which suggests that immune checkpoint inhibitors can enhance the anti-tumor immunity induced by the immunotoxin to restrict the tumor growth in the remote area.

The invention claimed is:

1. A method of treating a glioma tumor in a patient, comprising:
    administering to the patient an immunotoxin comprising a single chain variable region antibody fused to a PE38 truncated *Pseudomonas* exotoxin, wherein the single chain variable region antibody has CDR1, CDR2, and CDR3 regions as shown in SEQ ID NO: 6-11; and
    administering an inhibitor of an immune checkpoint to the patient, wherein the immune checkpoint is selected from the group consisting of PD-1 and CTLA-4.

2. The method of claim 1 wherein the tumor is a malignant glioma.

3. The method of claim 1 wherein the immunotoxin is administered directly to the tumor.

4. The method of claim 1 wherein the checkpoint inhibitor is an anti-PD-1 antibody.

5. The method of claim 1 wherein the checkpoint inhibitor is an anti-CTLA4 antibody.

6. The method of claim 1 wherein the immune checkpoint inhibitor is administered within 30 days of administering the immunotoxin.

7. The method of claim 1 wherein the immune checkpoint inhibitor is administered within 7 days of administering the immunotoxin.

8. The method of claim 1 wherein the PE38 truncated *Pseudomonas* exotoxin is fused to a KDEL peptide.

9. A kit for treating a glioma tumor, comprising:
    an immunotoxin comprising a single chain variable region antibody fused to a PE38 truncated *Pseudomonas* exotoxin, wherein the single chain variable region antibody has CDR1, CDR2, and CDR3 regions as shown in SEQ ID NO: 6-11; and
    an inhibitor of an immune checkpoint, wherein the immune checkpoint is selected from the group consisting of PD-1 and CTLA-4.

10. The kit of claim 9 wherein the checkpoint inhibitor is an anti-PD-1 antibody.

11. The kit of claim 9 wherein the checkpoint inhibitor is an anti-CTLA4 antibody.

12. The kit of claim 9 wherein the PE38 truncated *Pseudomonas* exotoxin is fused to a KDEL peptide.

13. The method of claim 1 wherein the immunotoxin comprises the amino acid sequence of SEQ ID NO: 1.

14. The method of claim 1 wherein the immunotoxin comprises the amino acid sequence of SEQ ID NO: 2.

15. The method of claim 1 wherein the immunotoxin comprises the amino acid sequence of SEQ ID NO: 3.

16. The method of claim 1 wherein the immunotoxin comprises the amino acid sequence of SEQ ID NO: 4.

17. The method of claim 1 wherein the immunotoxin comprises the amino acid sequence of SEQ ID NO: 5.

18. The kit of claim 9 wherein the immunotoxin comprises the amino acid sequence of SEQ ID NO: 1.

19. The kit of claim 9 wherein the immunotoxin comprises the amino acid sequence of SEQ ID NO: 2.

20. The kit of claim 9 wherein the immunotoxin comprises the amino acid sequence of SEQ ID NO: 3.

21. The kit of claim 9 wherein the immunotoxin comprises the amino acid sequence of SEQ ID NO: 4.

22. The kit of claim 9 wherein the immunotoxin comprises the amino acid sequence of SEQ ID NO: 5.

* * * * *

SEQUENCE LISTING

<160> NUMBER OF SEQ ID NOS: 14

<210> SEQ ID NO 1
<211> LENGTH: 120
<212> TYPE: PRT
<213> ORGANISM: Artificial Sequence
<220> FEATURE:
<223> OTHER INFORMATION: antibody construct, whole or portion
<223> OTHER INFORMATION: D2C7 VH

<400> SEQUENCE: 1

Glu Val His Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser Asn Gly Lys Cys Leu Glu Trp Ile
        35                  40                  45

Gly Asn Ile Asp Pro Tyr Tyr Gly Asp Thr Asp Tyr Asp Gln Lys Phe
    50                  55                  60

Lys Gly Lys Ala Thr Leu Thr Ala Asp Lys Ser Ser Asn Thr Val Tyr
65                  70                  75                  80

Met Gln Leu Gln Ser Leu Thr Ser Glu Asp Ser Ala Val Tyr Tyr Cys
                85                  90                  95

Ala Arg Gly Ala His Arg Asp Tyr Tyr Ala Met Asp Tyr Trp Gly Gln
            100                 105                 110

Gly Thr Ser Val Thr Val Ser Ser
        115                 120

<210> SEQ ID NO 2
<211> LENGTH: 15
<212> TYPE: PRT
<213> ORGANISM: Artificial Sequence
<220> FEATURE:
<223> OTHER INFORMATION: antibody construct, whole or portion
<223> OTHER INFORMATION: amino acid linker

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 107
<212> TYPE: PRT
<213> ORGANISM: Artificial Sequence
<220> FEATURE:
<223> OTHER INFORMATION: antibody construct, whole or portion
<223> OTHER INFORMATION: D2C7 VL

<400> SEQUENCE: 3

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Ile Tyr Ile Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Gly Leu Gln Pro
65                  70                  75                  80

Glu Asp Phe Gly Gly Tyr Tyr Cys Gln Gln His Tyr Gly Thr Pro Tyr
                85                  90                  95

Thr Phe Gly Cys Gly Thr Lys Leu Glu Lys Lys
            100                 105

<210> SEQ ID NO 4
<211> LENGTH: 351
<212> TYPE: PRT
<213> ORGANISM: Artificial Sequence
<220> FEATURE:
<223> OTHER INFORMATION: antibody construct, whole or portion
<223> OTHER INFORMATION: PE38KDEL

<400> SEQUENCE: 4

Lys Ala Ser Gly Gly Pro Glu Gly Gly Ser Leu Ala Ala Leu Thr Ala
1               5                   10                  15

His Gln Ala Cys His Leu Pro Leu Glu Thr Phe Thr Arg His Arg Gln
            20                  25                  30

Pro Arg Gly Trp Glu Gln Leu Glu Gln Cys Gly Tyr Pro Val Gln Arg
        35                  40                  45

Leu Val Ala Leu Tyr Leu Ala Ala Arg Leu Ser Trp Asn Gln Val Asp
    50                  55                  60

Gln Val Ile Arg Asn Ala Leu Ala Ser Pro Gly Ser Gly Gly Asp Leu
65                  70                  75                  80

Gly Glu Ala Ile Arg Glu Gln Pro Glu Gln Ala Arg Leu Ala Leu Thr

```
                85                  90                  95
Leu Ala Ala Ala Glu Ser Glu Arg Phe Val Arg Gln Gly Thr Gly Asn
            100                 105                 110

Asp Glu Ala Gly Ala Ala Asn Gly Pro Ala Asp Ser Gly Asp Ala Leu
            115                 120                 125

Leu Glu Arg Asn Tyr Pro Thr Gly Ala Glu Phe Leu Gly Asp Gly Gly
        130                 135                 140

Asp Val Ser Phe Ser Thr Arg Gly Thr Gln Asn Trp Thr Val Glu Arg
145                 150                 155                 160

Leu Leu Gln Ala His Arg Gln Leu Glu Glu Arg Gly Tyr Val Phe Val
                165                 170                 175

Gly Tyr His Gly Thr Phe Leu Glu Ala Ala Gln Ser Ile Val Phe Gly
            180                 185                 190

Gly Val Arg Ala Arg Ser Gln Asp Leu Asp Ala Ile Trp Arg Gly Phe
        195                 200                 205

Tyr Ile Ala Gly Asp Pro Ala Leu Ala Tyr Gly Tyr Ala Gln Asp Gln
    210                 215                 220

Glu Pro Asp Ala Arg Gly Arg Ile Arg Asn Gly Ala Leu Leu Arg Val
225                 230                 235                 240

Tyr Val Pro Arg Ser Ser Leu Pro Gly Phe Tyr Arg Thr Ser Leu Thr
                245                 250                 255

Leu Ala Ala Pro Glu Ala Ala Gly Glu Val Glu Arg Leu Ile Gly His
            260                 265                 270

Pro Leu Pro Leu Arg Leu Asp Ala Ile Thr Gly Pro Glu Glu Glu Gly
        275                 280                 285

Gly Arg Leu Glu Thr Ile Leu Gly Trp Pro Leu Ala Glu Arg Thr Val
    290                 295                 300

Val Ile Pro Ser Ala Ile Pro Thr Asp Pro Arg Asn Val Gly Gly Asp
305                 310                 315                 320

Leu Asp Pro Ser Ser Ile Pro Asp Lys Glu Gln Ala Ile Ser Ala Leu
                325                 330                 335

Pro Asp Tyr Ala Ser Gln Pro Gly Lys Pro Pro Lys Asp Glu Leu
            340                 345                 350

<210> SEQ ID NO 5
<211> LENGTH: 593
<212> TYPE: PRT
<213> ORGANISM: Artificial Sequence
<220> FEATURE:
<223> OTHER INFORMATION: antibody construct, whole or portion
<223> OTHER INFORMATION: D2C7-(scdsFv)-PE38KDEL

<400> SEQUENCE: 5

Glu Val His Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser Asn Gly Lys Cys Leu Glu Trp Ile
        35                  40                  45

Gly Asn Ile Asp Pro Tyr Tyr Gly Asp Thr Tyr Asp Gln Lys Phe
    50                  55                  60

Lys Gly Lys Ala Thr Leu Thr Ala Asp Lys Ser Ser Asn Thr Val Tyr
65                  70                  75                  80

Met Gln Leu Gln Ser Leu Thr Ser Glu Asp Ser Ala Val Tyr Tyr Cys
                85                  90                  95
```

```
Ala Arg Gly Ala His Arg Asp Tyr Tyr Ala Met Asp Tyr Trp Gly Gln
            100                 105                 110

Gly Thr Ser Val Thr Val Ser Ser Gly Gly Gly Ser Gly Gly Gly
        115                 120                 125

Gly Ser Gly Gly Gly Ser Asp Ile Gln Met Thr Gln Ser Pro Ala
    130                 135                 140

Ser Leu Ser Ala Ser Val Gly Glu Thr Val Thr Ile Thr Cys Arg Thr
145                 150                 155                 160

Ser Glu Asn Ile Tyr Ile Tyr Leu Ala Trp Tyr Gln Gln Lys Gln Gly
                165                 170                 175

Lys Ser Pro Gln Leu Leu Val Tyr Asn Ala Lys Thr Leu Ala Glu Gly
            180                 185                 190

Val Pro Ser Arg Phe Ser Gly Ser Gly Ser Gly Thr Gln Phe Ser Leu
        195                 200                 205

Lys Ile Asn Gly Leu Gln Pro Glu Asp Phe Gly Gly Tyr Tyr Cys Gln
    210                 215                 220

Gln His Tyr Gly Thr Pro Tyr Thr Phe Gly Cys Gly Thr Lys Leu Glu
225                 230                 235                 240

Lys Lys Lys Ala Ser Gly Gly Pro Glu Gly Gly Ser Leu Ala Ala Leu
                245                 250                 255

Thr Ala His Gln Ala Cys His Leu Pro Leu Glu Thr Phe Thr Arg His
            260                 265                 270

Arg Gln Pro Arg Gly Trp Glu Gln Leu Glu Gln Cys Gly Tyr Pro Val
        275                 280                 285

Gln Arg Leu Val Ala Leu Tyr Leu Ala Ala Arg Leu Ser Trp Asn Gln
    290                 295                 300

Val Asp Gln Val Ile Arg Asn Ala Leu Ala Ser Pro Gly Ser Gly Gly
305                 310                 315                 320

Asp Leu Gly Glu Ala Ile Arg Glu Gln Pro Glu Gln Ala Arg Leu Ala
                325                 330                 335

Leu Thr Leu Ala Ala Ala Glu Ser Glu Arg Phe Val Arg Gln Gly Thr
            340                 345                 350

Gly Asn Asp Glu Ala Gly Ala Ala Asn Gly Pro Ala Asp Ser Gly Asp
        355                 360                 365

Ala Leu Leu Glu Arg Asn Tyr Pro Thr Gly Ala Glu Phe Leu Gly Asp
    370                 375                 380

Gly Gly Asp Val Ser Phe Ser Thr Arg Gly Thr Gln Asn Trp Thr Val
385                 390                 395                 400

Glu Arg Leu Leu Gln Ala His Arg Gln Leu Glu Glu Arg Gly Tyr Val
                405                 410                 415

Phe Val Gly Tyr His Gly Thr Phe Leu Glu Ala Ala Gln Ser Ile Val
            420                 425                 430

Phe Gly Gly Val Arg Ala Arg Ser Gln Asp Leu Asp Ala Ile Trp Arg
        435                 440                 445

Gly Phe Tyr Ile Ala Gly Asp Pro Ala Leu Ala Tyr Gly Tyr Ala Gln
    450                 455                 460

Asp Gln Glu Pro Asp Ala Arg Gly Arg Ile Arg Asn Gly Ala Leu Leu
465                 470                 475                 480

Arg Val Tyr Val Pro Arg Ser Ser Leu Pro Gly Phe Tyr Arg Thr Ser
                485                 490                 495

Leu Thr Leu Ala Ala Pro Glu Ala Ala Gly Glu Val Glu Arg Leu Ile
            500                 505                 510

Gly His Pro Leu Pro Leu Arg Leu Asp Ala Ile Thr Gly Pro Glu Glu
```

```
            515                 520                 525
Glu Gly Gly Arg Leu Glu Thr Ile Leu Gly Trp Pro Leu Ala Glu Arg
    530                 535                 540

Thr Val Val Ile Pro Ser Ala Ile Pro Thr Asp Pro Arg Asn Val Gly
545                 550                 555                 560

Gly Asp Leu Asp Pro Ser Ser Ile Pro Asp Lys Glu Gln Ala Ile Ser
                565                 570                 575

Ala Leu Pro Asp Tyr Ala Ser Gln Pro Gly Lys Pro Pro Lys Asp Glu
            580                 585                 590

Leu

<210> SEQ ID NO 6
<211> LENGTH: 5
<212> TYPE: PRT
<213> ORGANISM: Artificial Sequence
<220> FEATURE:
<223> OTHER INFORMATION: antibody construct, whole or portion
<223> OTHER INFORMATION: VH, CDR1

<400> SEQUENCE: 6

Gly Tyr Asn Met Asn
1               5

<210> SEQ ID NO 7
<211> LENGTH: 17
<212> TYPE: PRT
<213> ORGANISM: Artificial Sequence
<220> FEATURE:
<223> OTHER INFORMATION: antibody construct, whole or portion
<223> OTHER INFORMATION: VH, CDR2

<400> SEQUENCE: 7

Asn Ile Asp Pro Tyr Tyr Gly Asp Thr Asp Tyr Asp Gln Lys Phe Lys
1               5                   10                  15

Gly

<210> SEQ ID NO 8
<211> LENGTH: 11
<212> TYPE: PRT
<213> ORGANISM: Artificial Sequence
<220> FEATURE:
<223> OTHER INFORMATION: antibody construct, whole or portion
<223> OTHER INFORMATION: VH, CDR3

<400> SEQUENCE: 8

Gly Ala His Arg Asp Tyr Tyr Ala Met Asp Tyr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: antibody construct, whole or portion
<223> OTHER INFORMATION: VL, CDR1

<400> SEQUENCE: 9

Arg Thr Ser Glu Asn Ile Tyr Ile Tyr Leu Ala
1               5                   10

<210> SEQ ID NO 10
<211> LENGTH: 7
<212> TYPE: PRT
<213> ORGANISM: Artificial Sequence
```

<220> FEATURE:
<223> OTHER INFORMATION: antibody construct, whole or portion
<223> OTHER INFORMATION: VL, CDR2

<400> SEQUENCE: 10

Asn Ala Lys Thr Leu Ala Glu
1               5

<210> SEQ ID NO 11
<211> LENGTH: 9
<212> TYPE: PRT
<213> ORGANISM: Artificial Sequence
<220> FEATURE:
<223> OTHER INFORMATION: antibody construct, whole or portion
<223> OTHER INFORMATION: VL, CDR3

<400> SEQUENCE: 11

Gln Gln His Tyr Gly Thr Pro Tyr Thr
1               5

<210> SEQ ID NO 12
<211> LENGTH: 1779
<212> TYPE: DNA
<213> ORGANISM: Artificial Sequence
<220> FEATURE:
<223> OTHER INFORMATION: antibody construct, whole or portion
<223> OTHER INFORMATION: D2C7-(scdsFv)-PE38KDEL

<400> SEQUENCE: 12

```
gaggtccacc tgcagcagtc tggacctgag ctggagaagc ctggcgcttc agtgaagata      60
tcctgcaagg cttctggtta ctcattcact ggctacaaca tgaactgggt gaagcagagc     120
aatggcaagt gccttgagtg gattggaaat attgatcctt actatggtga tactgactac     180
gaccagaagt tcaagggcaa ggccacattg actgcagaca atcctccaa cacagtctac      240
atgcagctcc agagcctgac atctgaggac tctgcagtct attactgtgc aagaggggcc     300
catagggatt actatgctat ggactactgg ggtcaaggga cctcagtcac cgtctcctca     360
ggtggtggcg gttcaggcgg aggtggctct ggcggtggcg gatcggacat ccagatgact     420
cagtctccag cctccctatc tgcatctgtg ggagaaactg tcaccatcac atgtcgaaca     480
agtgagaata tttacattta tttagcatgg tatcagcaga acagggaaa atctcctcag      540
ctcctggtct ataatgcaaa aaccttagca gaaggtgtgc catcaaggtt cagtggcagt     600
gggtcaggca cacagttttc tctgaagatc aacggcctgc agcctgaaga ttttggggt      660
tattactgtc aacagcatta tggcactccg tacacgttcg gatgcgggac caagctggaa     720
aaaaaaaaag cttccggagg tcccgagggc ggcagcctgg ccgcgctgac cgcgcaccag     780
gcttgccacc tgccgctgga ctttcacc cgtcatcgcc agccgcgcgg ctgggaacaa     840
ctggagcagt gcggctatcc ggtgcagcgg ctggtcgccc tctacctggc ggcgcggctg     900
tcgtggaacc aggtcgacca ggtgatccgc aacgccctgg ccagcccgg cagcggcggc     960
gacctgggcg aagcgatccg cgagcagccg gagcaagccc gtctggccct gaccctggcc    1020
gccgccgaga gcgagcgctt cgtccggcag ggcaccggca acgacgaggc cggcgcggcc    1080
aacgccccgg cggacagcgg cgacgccctg ctggagcgca actatcccac tggcgcggag    1140
ttcctcggcg acggcggcga cgtcagcttc agcacccgcg gcacgcagaa ctggacggtg    1200
gagcggctgc tccaggcgca ccgccaactg gaggagcgcg gctatgtgtt cgtcggctac    1260
cacggcaccc tcctgaaagc ggcgcaaagc atcgtcttcg gcgggggtgcg cgcgcgcagc    1320
caggacctcg acgcgatctg gcgcggtttc tatatcgccg gcgatccggc gctggcctac    1380
```

| | |
|---|---|
| ggctacgccc aggaccagga acccgacgca cgcggccgga tccgcaacgg tgccctgctg | 1440 |
| cgggtctatg tgccgcgctc gagcctgccg ggcttctacc gcaccagcct gaccctggcc | 1500 |
| gcgccggagg cggcgggcga ggtcgaacgg ctgatcggcc atccgctgcc gctgcgcctg | 1560 |
| gacgccatca ccggccccga ggaggaaggc gggcgcctgg agaccattct cggctggccg | 1620 |
| ctggccgagc gcaccgtggt gattccctcg gcgatcccca ccgacccgcg caacgtcggc | 1680 |
| ggcgacctcg acccgtccag catccccgac aaggaacagg cgatcagcgc cctgccggac | 1740 |
| tacgccagcc agcccggcaa accgccgaaa gacgagctc | 1779 |

<210> SEQ ID NO 13
<211> LENGTH: 726
<212> TYPE: DNA
<213> ORGANISM: Artificial Sequence
<220> FEATURE:
<223> OTHER INFORMATION: antibody construct, whole or portion
<223> OTHER INFORMATION: D2C7-(scdsFv)

<400> SEQUENCE: 13

| | |
|---|---|
| gaggtccacc tgcagcagtc tggacctgag ctggagaagc ctggcgcttc agtgaagata | 60 |
| tcctgcaagg cttctggtta ctcattcact ggctacaaca tgaactgggt gaagcagagc | 120 |
| aatggcaagt gccttgagtg gattggaaat attgatcctt actatggtga tactgactac | 180 |
| gaccagaagt tcaagggcaa ggccacattg actgcagaca atcctccaa cacagtctac | 240 |
| atgcagctcc agagcctgac atctgaggac tctgcagtct attactgtgc aagaggggcc | 300 |
| catagggatt actatgctat ggactactgg ggtcaaggga cctcagtcac cgtctcctca | 360 |
| ggtggtggcg gttcaggcgg aggtggctct ggcggtggcg gatcggacat ccagatgact | 420 |
| cagtctccag cctccctatc tgcatctgtg ggagaaactg tcaccatcac atgtcgaaca | 480 |
| agtgagaata tttacattta tttagcatgg tatcagcaga acagggaaa atctcctcag | 540 |
| ctcctggtct ataatgcaaa aaccttagca gaaggtgtgc catcaaggtt cagtggcagt | 600 |
| gggtcaggca cacagttttc tctgaagatc aacgcctgc agcctgaaga ttttgggggt | 660 |
| tattactgtc aacagcatta tggcactccg tacacgttcg gatgcgggac caagctggaa | 720 |
| aaaaaa | 726 |

<210> SEQ ID NO 14
<211> LENGTH: 1053
<212> TYPE: DNA
<213> ORGANISM: Artificial Sequence
<220> FEATURE:
<223> OTHER INFORMATION: antibody construct, whole or portion
<223> OTHER INFORMATION: PE38KDEL

<400> SEQUENCE: 14

| | |
|---|---|
| aaagcttccg gaggtcccga gggcggcagc ctggccgcgc tgaccgcgca ccaggcttgc | 60 |
| cacctgccgc tggagacttt cacccgtcat cgccagccgc gcggctggga caactggag | 120 |
| cagtgcggct atccggtgca gcggctggtc gccctctacc tggcggcgcg gctgtcgtgg | 180 |
| aaccaggtcg accaggtgat ccgcaacgcc ctggccagcc ccggcagcgg cggcgacctg | 240 |
| ggcgaagcga tccgcgagca gccggagcaa gcccgtctgg ccctgaccct ggccgccgcc | 300 |
| gagagcgagc gcttcgtccg gcagggcacc ggcaacgacg aggccggcgc ggccaacggc | 360 |
| ccggcggaca gcggcgacgc cctgctggag cgcaactatc ccactggcgc ggagttcctc | 420 |
| ggcgacggcg gcgacgtcag cttcagcacc cgcggcacgc agaactggac ggtggagcgg | 480 |

-continued

```
ctgctccagg cgcaccgcca actggaggag cgcggctatg tgttcgtcgg ctaccacggc    540
accttcctcg aagcggcgca aagcatcgtc ttcggcgggg tgcgcgcgcg cagccaggac    600
ctcgacgcga tctggcgcgg tttctatatc gccggcgatc cggcgctggc ctacggctac    660
gcccaggacc aggaacccga cgcacgcggc cggatccgca acggtgccct gctgcgggtc    720
tatgtgccgc gctcgagcct gccgggcttc taccgcacca gcctgaccct ggccgcgccg    780
gaggcggcgg gcgaggtcga acggctgatc ggccatccgc tgccgctgcg cctggacgcc    840
atcaccggcc ccgaggagga aggcgggcgc ctggagacca ttctcggctg gccgctggcc    900
gagcgcaccg tggtgattcc ctcggcgatc cccaccgacc cgcgcaacgt cggcggcgac    960
ctcgacccgt ccagcatccc cgacaaggaa caggcgatca gcgccctgcc ggactacgcc    1020
agccagcccg gcaaaccgcc gaaagacgag ctc                                 1053
```